United States Patent [19]

Lyga et al.

[11] Patent Number: 4,906,287
[45] Date of Patent: Mar. 6, 1990

[54] HERBICIDAL COMPOUNDS

[75] Inventors: John W. Lyga, Basking Ridge; George Theodoridis, Princeton; Lester L. Maravetz, Westfield, all of N.J.

[73] Assignee: FMC Corporation, Philadelphia, Pa.

[21] Appl. No.: 22,556

[22] Filed: Mar. 5, 1987

Related U.S. Application Data

[63] Continuation of Ser. No. 856,628, Apr. 25, 1986, abandoned, which is a continuation-in-part of Ser. No. 807,790, Dec. 12, 1985, Pat. No. 4,766,233, which is a continuation-in-part of Ser. No. 755,749, Jul. 2, 1985, abandoned, which is a continuation-in-part of Ser. No. 619,880, Jun. 12, 1984, abandoned.

[51] Int. Cl.$^4$ .................. A01N 43/707; C07D 253/06; C07D 417/10
[52] U.S. Cl. .......................... 71/93; 71/91; 544/3; 544/182; 540/544
[58] Field of Search .................. 544/182, 3; 71/93, 91; 540/544

[56] References Cited

U.S. PATENT DOCUMENTS

| | | | |
|---|---|---|---|
| 3,544,570 | 12/1970 | Timmler et al. | 544/182 |
| 3,560,497 | 2/1971 | Miller | 544/182 |
| 3,671,523 | 6/1972 | Westphal et al. | 544/182 |
| 3,852,289 | 12/1974 | Mylari et al. | 544/182 |
| 3,882,115 | 5/1975 | Mylari | 544/182 |
| 3,883,525 | 5/1975 | Mylari | 544/182 |
| 3,883,527 | 5/1975 | Brennan | 544/182 |
| 3,883,528 | 5/1975 | Mylari | 544/182 |
| 3,896,124 | 7/1975 | Mylari | 544/182 |
| 3,905,971 | 9/1975 | Miller | 544/182 |
| 3,912,723 | 10/1975 | Miller | 544/182 |
| 4,058,525 | 11/1977 | Hofer et al. | 544/182 |
| 4,198,407 | 4/1980 | Rosner et al. | 544/182 |
| 4,318,731 | 3/1982 | Kajioka et al. | 71/92 |
| 4,404,019 | 9/1983 | Uematsu et al. | 71/92 |
| 4,427,438 | 1/1984 | Nagano et al. | 71/92 |
| 4,431,822 | 2/1984 | Nagano et al. | 548/513 |
| 4,439,229 | 3/1984 | Swithenbank | 71/96 |
| 4,452,981 | 6/1984 | Nagano et al. | 544/236 |
| 4,640,917 | 2/1987 | Rosner et al. | 514/222 |

FOREIGN PATENT DOCUMENTS

| | | |
|---|---|---|
| 0011693 | 6/1980 | European Pat. Off. . |
| 49508 | 4/1982 | European Pat. Off. . |
| 49511 | 4/1982 | European Pat. Off. . |
| 83055 | 7/1983 | European Pat. Off. . |
| 275131 | 7/1988 | European Pat. Off. . |
| 2606850 | 9/1977 | Fed. Rep. of Germany . |
| 3016304 | 11/1980 | Fed. Rep. of Germany . |
| 3531919 | 3/1987 | Fed. Rep. of Germany ...... 544/182 |
| WO87/07602 | 12/1987 | PCT Int'l Appl. . |
| 1371907 | 10/1974 | United Kingdom . |
| 2071100 | 9/1981 | United Kingdom . |
| 8501637 | 4/1985 | World Int. Prop. O. . |
| 8501939 | 5/1985 | World Int. Prop. O. . |

OTHER PUBLICATIONS

F. Yoneda et al., "Synthesis of 6-Aryl-1,3-Dimethyl-6,7-Dihydro-6-Azalumazin-7-(6H)-Ones and Their Conversion into 2-Aryl-1,2,4-Triazine-3,-5-(2H,4H) Diones. A New Synthesis of 1-Aryl-6-Azauracils", J. Heterocycl. Chem., 17, 1365-1368 (1980).

M. W. Miller et al., "Anticoccidial Derivatives of 6-Azauracil. 4. A1000 Fold Enhancement of Potency by Phenyl Sulfide and Phenyl Sulfone Side Chains", J. Med.-Chem., 24, 1337-1342 (1981).

P. Winternitz, "Preparation of Substituted 2,3,4,5-Tetrahydro-1,2,4-Triazine-6-Carbonitriles and Some of its Derivatives", Helv.Chem.Acta., 61, 1175-1185 (1978); C.A. 89: 4334t (1978).

M. W. Miller et al., "Anticoccidial Derivatives of 6-Azauracil. 2.High Potency and Long Plasma Life of N1-Phenyl Structures", J. Med. Chem., 22, 1483-1487 (1979).

J. Slouka et al., "1-Aryl-6-Azauracils XX. 1-Aryl-6-Azauracils Hydrolytic Ring Opening", Acta Univ. Palacki. Olomuc., Fac. Rerum Nat., 45, 113-120 (1974); C.A. 82: 125360s (1975).

B. L. Mylari et al., "Anticoccidal Derivatives of 6-Azauracil. 1. Enhancement of Activity by Benzylation of Nitrogen-1.Observations on the Design of Nucleotide Analogues in Chemotherapy", J. Med. Chem., 20, 475-483 (1977).

Primary Examiner—John M. Ford
Attorney, Agent, or Firm—Robert M. Kennedy; H. Robinson Ertelt; Beverly K. Johnson

[57] ABSTRACT

Herbicidal 2-aryl-1,2,4-triazine-3,5(2H,4H)-diones, the corresponding 2-aryldihydro-1,2,4-triazine-3,5-diones and sulfur analogs of said diones.

14 Claims, No Drawings

HERBICIDAL COMPOUNDS

This application is a continuation of Ser. No. 856,628, filed Apr. 25, 1986, now abandoned, which is a continuation-in-part of application Ser. No. 807,790, filed Dec. 12, 1985, now U.S. Pat. No. 4,766,233, which is a continuation-in-part of application Ser. No. 755,749, filed July 2, 1985, now abandoned, which is a continuation-in-part of application Ser. No. 619,880, filed June 12, 1984, now abandoned.

The invention described in this application pertains to weed control in agriculture, horticulture, and other fields where there is a desire to control unwanted plant growth. More specifically, the present application describes herbicidal 2-aryl-1,2,4-triazine-3,5(2H,4H)-diones, the corresponding 2-aryldihydro-1,2,4-triazine-3,5-diones and sulfur analogs of said diones, compositions of them, methods of preparing them, and methods for preventing or destroying undesired plant growth by preemergence or postemergence application of the heribicdal compositions to the locus where control is desired. The present compounds may be used to effectively control a variety of both grassy and broadleaf plant species. The present invention is particularly useful in agriculture, as a number of the compounds described herein show a selectivity favorable to soybean, corn, cotton, cereal crops such as wheat, upland rice or paddy rice, or other crops at application levels which prevent the growth of or destroy a variety of weeds.

Herbicidal 2-aryl-1,2,4-triazine-3,5(2H,4H)-diones and sulfur analogs thereof are disclosed in parent application Ser. No. 807,790 filed Dec. 12, 1985, (of which the present application is a continuation-in-part), which is a continuation-in-part of application Ser. No. 755,749 filed July 2, 1985 which is in turn a continuation-in-part of application Ser. No. 619,880 filed June 12, 1984, and in published International (PCT) application WO 86/00072 published Jan. 3, 1986. All of said applications are incorporated herein by reference. The present application contains additional disclosure as to the 2-aryl-1,2,4-triazine-3,5-(2H,4H)-diones and processes for their manufacture, and also discloses the corresponding dihydrotriazinediones and their use as herbicidal compounds. 1,2,4-Triazine-3,5(2H,4H)-diones as a class are generally associated with the pharmaceutical or animal health arts and are commonly referred to therein as 6-azauracils. Such compounds, however, are relatively unknown in the herbicide art. Herbicidal activity is disclosed in German Offenlegungschrift No. 3,016,304 for optionally substituted triazinediones having the formula

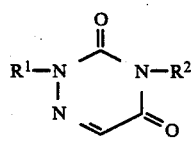

wherein $R^1$ is hydrogen, hydroxymethyl or an ester derivative thereof such as a benzoic acid ester, optionally substituted aminomethyl, optionally halosubstituted 2-tetrahydrofuranyl, 2-(2H,5H)dihydrofuranyl, or 2-tetrahydropyranyl, and $R^2$ is hydrogen, an optionally substituted aminomethyl, optionally halo-substituted 2-tetrahydrofuranyl, or 2-tetrahydropyranyl, with certain provisos; and for dihydrotriazolinones having the formula

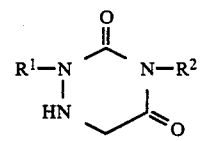

where $R^1$ is hydrogen, a hydroxymethyl ester derivative such as benzoic acid ester, 2-tetrahydrofuranyl or 2-tetrahydropyranyl, and $R^2$ is hydrogen, 2-tetrahydrofuranyl or 2-tetrahydropyranyl, with certain provisos.

European published patent application 0 011 693 of 1979 refers to phenyltriazinediones having a —NHSO$_2$CF$_3$ substituent on the phenyl group. The compounds of the present invention do not require such a substituent for their herbicidal effects.

It has been discovered that 2-aryl-1,2,4-triazine-3,5-(2H,4H)-diones the corresponding 2-aryldihydro-1,2,4-triazine-3,5-diones and sulfur analogs of said diones have herbicidal properties and may be used effectively either preemergently or postemergently for herbicidal purposes.

The herbicidal compounds of this invention have the formula

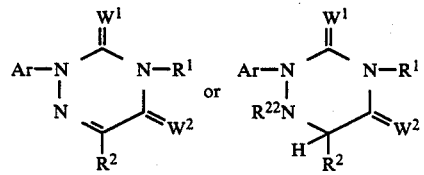

where Ar is an aryl radical, preferably a ring-substituted aryl radical. For instance it may have a benzene ring such as the radical indicated by the following formula

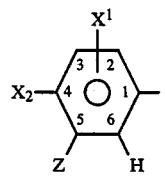

wherein $X^1$ may be for instance hydrogen or halogen, preferably fluorine or chlorine, the halogen atom advantageously being positioned at the C-2 carbon atom of the phenyl ring;

$X^2$ may be hydrogen, halogen such as fluorine, chlorine, or bromine, alkyl of 1 to 6 (preferably 1 to 4) carbon atoms, particularly methyl, haloalkyl of 1 to 5 carbon atoms, for example, trifluoromethyl, alkoxy of 1 to 6 (preferably 1 to 4) carbon atoms, or phenoxy or phenylmethoxy which may be ring substituted with halogen or alkyl alkoxy of 1 to 4 carbon atoms;

Z may be hydrogen or, preferably, a substituent of group selected from fluorine, chlorine, bromine, iodine, cyano, nitro, amino, alkoxycarbonylamino of 1 to 6 (preferably 1 to 4) alkyl carbon atoms, di(alkylcarbonyl)amino in which each alkyl is of 1 to 6 (preferably 1 to 4) carbon atoms, hydroxysulfonyl, alkyl of 1 to 6 (preferably 1 to 4) carbon atoms, haloalkyl of 1 to 5 carbon atoms, —QR, —CO—R$^6$, —S(O)$_m$R$^8$, —Q$^2$R$^9$, —O-

$SO_2R^{10}$, $-NHN=CR^{11}R^{12}$, and $-Q-CR^3R^4-(CH_2)_n-CO-Q^1-R^5$.

For $Z=-QR$, Q may be O, S, or $NR^7$; $R^7$ may be hydrogen or alkyl of 1 to 6 (preferably 1 to 4) carbon atoms; and R may be alkyl of 1 to 6 (preferably 1 to 4) carbon atoms which may be substituted with cycloalkyl of 3 to 7 carbon atoms (for example, methyl, 1-methylethyl, or cyclohexylmethyl), cycloalkyl of 3 to 7 (preferably 5 or 6) carbon atoms which may be substituted with alkyl of 1 to 6 carbon atoms (for example, cyclopentyl or methylcyclopropyl), alkoxyalkyl of 2 to 8 (preferably 2 to 4) carbon atoms (for example, ethoxymethyl), alkoxyalkoxyalkyl of 3 to 8 (preferably 3 to 5) carbon atoms (for example, 2-methoxyethoxymethyl), alkylthioalkyl of 2 to 8 (preferably 2 to 4) carbon atoms or the sulfinyl or sulfonyl derivative thereof, tri(alkyl of 1 to 4 carbon atoms)silyl(alkyl of 1 to 4 carbon atoms) such as trimethylsilylmethyl, cyanoalkyl of 1 to 5 (preferably 1 to 3) alkyl carbon atoms such as cyanomethyl or 2-cyanoethyl, alkenyl of 2 to 5 (preferably 3 to 5) carbon atoms such as 2-propenyl, alkynyl of 2 to 5 (preferably 3 to 5) carbon atoms such as 2-propynyl, haloalkyl of 1 to 5 (preferably 1 to 3) carbon atoms especially a fluoralkyl, haloalkenyl of 2 to 5 (preferably 3 to 5) carbon atoms, haloalkynyl of 2 to 5 (preferably 3 to 5) carbon atoms such as 3-bromo-2-propynyl, alkylcarbonyl of 1 to 6 (preferably 1 to 4) alkyl carbon atoms such as acetyl, or dialkylaminocarbonyl or dialkylaminothiocarbonyl in which each alkyl is of 1 to 6 (preferably 1 to 4) carbon atoms.

The compounds in which $Z=-QR$, especially where $X^1$ is 2-F and $X^2$ is Cl or Br, form a preferred embodiment of the invention; particularly where Q is sulfur, more particularly where Q is oxygen. Frequently, R will be selected from among alkyl, cyanoalkyl, alkynyl, haloalkynyl, and alkoxyalkyl. Typical such R groups include, for example, 1-methylethyl, cyanomethyl, 2-propynyl, 3-bromo-2-propynyl, and methoxymethyl. Preferably R will be 1-methylethyl or, especially, 2-propynyl or methoxymethyl.

In another preferred embodiment where $Z=-QR$ and is $-NR^7$, Z is $-N(R^{21})SO_2R^{20}$, in which $R^{20}$ may be alkyl (such as straight chain or branched chain lower alkyl, e.g. methyl, ethyl, propyl), less preferably it may be haloalkyl other than $CF_3$ (e.g. $CH_2F$ or $CHF_2$) or aryl (such as phenyl, optionally substituted with one or more of: halogen such as Cl, Br or F; alkyl such as lower alkyl, e.g. methyl; alkoxy such as lower alkoxy, e.g. methoxy; cyano; cyanomethyl; nitro; amino; arylamino such as phenylamino; mono- and dialkylamino such as methylamino or dimethylamino; carboxyl; alkoxycarbonyl such as $-COOC_2H_5$; alkoxyalkyl such as alkoxymethyl of 2 to 4 carbon atoms; alkoxycarbonylalkyl such as $-CH_2COOC_2H_5$; benzyl; or hydroxy).

$R^{21}$ may be hydrogen, alkyl (e.g. straight or branched chain lower alkyl such as methyl, ethyl, propyl, isopropyl or butyl), benzyl, haloalkyl (e.g. $CFH_2$ or $CH_2CH_2CH_2F$), alkoxy (e.g. methoxy), $SO_2R^{20}$, alkynyl (such as propargyl) alkenyl (such as allyl), a group of the formula $-$alkylene$-SO_2R^{20}$ (in which, for example, said alkylene group (e.g. $-CH_2-$) has 1 to 4 carbon atoms, alkoxymethyl (such as methyloxymethyl), cyanomethyl or ethoxycarbonylmethyl.

$R^{20}$ and $R^{21}$ together may be a divalent radical such as alkylene (e.g. of 1 to 10 carbon atoms such as methylene or 1,3-propylene).

$R^{21}$ may also be a salt-forming group such as a metal (e.g. Na, K or Ca) or ammonium (e.g. $NH_4$ or lower alkyl-substituted ammonium).

For $Z=-CO-R^6$, $R^6$ may be hydroxy, alkoxy or alkylthio of 1 to 6 (preferably 1 to 4) carbon atoms such as methoxy or methylthio, alkoxyalkoxy of 2 to 6 (preferably 2 to 4) carbon atoms (for example, 2-methoxyethoxy), amino, or alkylamino or dialkylamino wherein each alkyl is of 1 to 6 (preferably 1 to 4) carbon atoms and may be substituted with alkoxy of 1 to 4 carbon atoms (for example, methylamino, dimethylamino, or methyl(2-methoxyethyl)amino). For example, Z, defined as $-CO-R^6$, may be $CO_2H$, $CO_2$alkyl, CO$-$S$-$alkyl, $CO_2$alkyl-O-alkyl, $CONH_2$, or CONH-alkyl or CON(alkyl)$_2$ in which any alkyl may be substituted with alkoxy. Compounds in which Z is $-CO-R^6$, especially where $X^1$ is 2-F and $X^2$ is Cl or Br, form a preferred embodiment of the invention. For $Z=-S(O)_mR^8$, m may be 1 or 2 and $R^8$ may be alkyl of 1 to 6 (preferably 1 to 4) carbon atoms or alkenyl or alkynyl of 2 to 5 (preferably 3 to 5) carbon atoms. For example, Z may be $-SO-CH_3$, $-SO_2CH(CH_3)_2$, $-SO_2CH_2CH=CH_2$, or $-SO-CH_2C=CH$.

For $Z=-Q^2R^9$, $Q^2$ may be sulfur or, preferably, oxygen, and $R^9$ may be a 5- or 6-membered ring heterocyclic group of 1 to 2 same or different (preferably the same) heteroatoms selected from O,S (including the S-oxide and S-dioxide), and N or an alkyl radical of 1 to 5 (preferably 1 to 3) carbon atoms substituted with said heterocyclic group. $R^9$ will frequently be (a) an optionally substituted and optionally benzene-adjoined nitrogen-containing heterocycle or an alkyl radical of 1 to 5 carbon atoms substituted with said heterocycle;

(b) an aromatic, optionally substituted and optionally benzene-adjoined, oxygen- or sulfur-containing heterocycle or an alkyl group of 1 to 5 carbon atoms substituted therewith; or, advantageously, (c) a non-aromatic, optionally substituted and optionally benzene-adjoined, oxygen- or sulfur-containing heterocycle or an alkyl group of 1 to 5 carbon atoms substituted therewith.

Examples of $R^9$ groups include 1-methyl-3-pyrrolidinyl, furfuryl, 2-thienylmethyl, 3-tetrahydrofuranyl, tetrahydrofurfuryl, tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahydrothiene-3-yl, 2,2-dimethyl-1,1,3,3-tetraoxo-1,3-dithiolan-4-ylmethyl, 1,1-dioxotetrahydro4H-thiopyran-4-yl, and 1,3-oxothiolan-2-ylmethyl.

For $Z=-OSO_2R^{10}$, $R^{10}$ may be alkyl of 1 to 6 (preferably 1 to 4) carbon atoms (which may be substituted with halogen, cyano, alkoxy or aklylthio of 1 to 4 carbon atoms, or alkylamino or dialkylamino in which alkyl is of 1 to 4 carbon atoms), phenyl, or alkylamino or dialkylamino in which alkyl is of 1 to 4 carbon atoms. Examples of such Z substituents include phenylsulfonyloxy, methylsulfonyloxy, ethylsulfonyloxy, propylsulfonyloxy, butylsulfonyloxy, 1-methylethylsulfonyloxy, 1-methylpropylsulfonyloxy, 2-methylpropylsulfonyloxy, 3-methylbutylsulfonyloxy, chloromethylsulfonyloxy, 3-chloropropylsulfonyloxy, trifluoromethylsulfonyloxy, methylaminosulfonyloxy, dimethylaminosulfonyloxy, dimethylaminoethylsulfonyloxy, 2-methoxyethylsulfonyloxy, 2-ethoxyethylsulfonyloxy, and cyanomethylsulfonyloxy.

For $Z=-NHN=C(R^{11})(R^{12})$, one of $R^{11}$ and $R^{12}$ may be hydrogen or alkyl of 1 to 4 carbon atoms and the other may be alkyl of 1 to 4 carbon atoms, or $C(R^{11})(R^{12})$ taken as a unit may be cycloalkyl of 3 to 7 (preferably 5 to 7) carbon atoms. For example, Z may be $NHN=C(CH_3)_2$, $NHN=CHCH_2CH_3$, $NHN=C(CH_3)(C_2H_5)$,

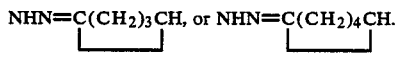

For

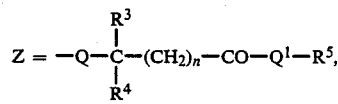

n may be 0 to 2, preferably 0; $R^3$ may be hydrogen or alkyl of 1 to 4 carbon atoms; $R^4$ may be hydrogen, alkyl of 1 to 4 carbon atoms, or alkoxy of 1 to 4 carbon atoms; Q and $Q^1$ may be independently O, S, or $NR^7$ in which $R^7$ is hydrogen or alkyl of 1 to 6 (preferably 1 to 4) carbon atoms; and $R^5$ may be hydrogen, alkyl of 1 to 6 (preferably 1 to 4) carbon atoms which may be substituted with cycloalkyl of 3 to 7 carbon atoms (for example, methyl, cyclopropylmethyl, cyclopentylmethyl, or cyclohexylmethyl, cycloalkyl of 3 to 7 carbon atoms which may be substituted with alkyl of 1 to 4 carbon atoms (for example, methylcyclopropyl, cyclopentyl, cyclohexyl, 2-methylcyclohexyl, or cycloheptyl), alkoxyalkyl or alkylthioalkyl of 2 to 6 carbon atoms, haloalkyl of 1 to 5 carbon atoms (especially fluoroalkyl or chloroalkyl), alkenyl of 2 to 5 carbon atoms such as 2-propenyl, cycloalkenyl of 5 to 7 carbon atoms which may be substituted with alkyl of 1 to 4 carbon atoms (for example, 2-cyclohexenyl), cycloalkenylalkyl of 6 to 10 carbon atoms (for example, 3-cyclohexenylmethyl), phenyl or phenylmethyl (each of which may be ring-substituted with fluorine, chlorine, bromine, or alkyl, alkoxy, or alkylthio of 1 to 4 carbon atoms), cyanoalkyl of 1 to 5 alkyl carbon atoms such as cyanomethyl, alkynyl of 2 to 5 carbon atoms such as 2-propynyl, alkylimino of 1 to 6 (preferably 1 to 4) carbon atoms which may be substituted with cycloalkyl of 3 to 7 carbon atoms, or cycloalkylimino of 5 to 7 carbon atoms which may be substituted with alkyl of 1 to 4 carbon atoms; or $Q^1$ and $R^5$ may together represent a phenylsulfonylamino group in which the phenyl is unsubstituted or substituted e.g. with halogen such as fluorine, chlorine, or bromine, alkyl of 1 to 4 carbon atoms, alkoxy of 1 to 4 carbon atoms, or alkoxycarbonyl of 1 to 4 alkyl carbon atoms.

This subgenus, especially where $X^1$ is 2-F and $X^2$ is Cl or Br, forms a preferred embodiment of the invention; particularly where n of 0 and one of $R^3$ and $R^4$ is H and the other is H, $CH_3$, $C_2H_5$, $OCH_3$, or $OC_2H_5$. Where Q or $Q^1$ is $NR^7$, $R^7$ is preferably H in this subgenus. Examples of Z substituents of this subgenus where Q is $NR^7$ include those of the formulas $-NHCH_2CO_2R^5$ and $-NHCH(CH_3)CO_2R^5$ where $R^5$ is methyl, ethyl, propyl, butyl, 2-methoxyethyl, 2-propoxyethyl, 2-cyanoethyl, 2,3-dichloropropyl, 2,2-dichloroethyl, cyclopentylmethyl, cyclopentyl, 1-methylethyl, 1-ethylpropyl, or 1-methylpropyl.

Thus, Z may be H or a substituent or group such as F, Cl, Br, I, $NO_2$, $NH_2$, CN, $SO_3H$, alkyl, haloalkyl, OR, SR, $NR^7R$, $NHCO_2$-alkyl, $N(CO-alkyl)_2$, $CO-R^6$, $SO-R^8$, $SO_2-R^8$, $OR^9$, $SR^9$, $OSO_2R^{10}$, $NHN=CR^{11}R^{12}$, $O-CR^3R^4-CO_2R^5$, $O-CR^3R^4-CO-SR^5$, $O-CR^3R^4-CO-NR^7R^5$, $O-CR^3R^4-CO_2R^5$, $S-CR^3R^4-CO-SR^5$, $S-CR^3R^4-CO-NR^7R^5$, $NR^7-CR^3R^4-CO_2R^5$, $NR^7-CR^3R^4-CO-SR^5$, or $NR^7-CR^3R^4-CO-NR^7R^5$.

In a preferred embodiment (including compounds particularly suitable for postemergence application to cereal crops) $Q^1R^5$ is the residue of a sulfonamide, of the formula $-NR^7R^5$ where $R^5$ may be, for instance, alkylsulfonyl, haloalkylsulfonyl, cycloaklylsulfonyl, arylsulfonyl (including heteroarylsulfonyl such as isooxazolylsulfonyl or thienylsulfonyl), aralkylsulfonyl, aminosulfonyl, dialkylaminosulfonyl, alkylaminosulfonyl, alkylthioalkylsulfonyl (e.g. $CH_3SCH_2SO_2-$), alkylsulfonylalkylsulfonyl (e.g. $CH_3SO_2CH_2SO_2-$) alkenylsulfonyl, phenylalkenylsulfonyl. Here $R^5$ may be bicyclic or polycyclic such as benzofuransulfonyl, dihydrobenzofuransulfonyl, naphthalenesulfonyl, benzodioxosulfonyl, anthraquinonesulfonyl or 1,4-naphthoquinonesulfonyl and $R^5$ may carry one or more substituents such as halogen, nitro, amino, fluorosulfonyl, alkyl, haloalkyl, aminoalkyl, dialkylaminoalkyl, haloalkoxy, alkoxy, alkenyloxy, haloalkenyloxy, alkynyloxy, cyanoalkoxy, epoxyalkoxy, dialkylaminoalkoxy, alkoxyalkoxy, alkoxyalkylthio, cyano, aminocarbonyloxy, alkylaminocarbonyloxy, dialkylaminocarbonyloxy, acylamino, alkoxycarbonyl, aminocarbonyl, alkylaminocarbonyl, dialkylaminocarbonyl, or hydroxycarbonyl; for instance, when $R^5$ is arylsulfonyl, the aryl radical of $R^5$ may be an unsubstituted phenyl or naphthyl or benzofuranyl or may be a phenyl or naphthyl or benzofuranyl carrying one or more of the foregoing substituents, with any alkyl portion of a substituent having, for instance, 1 to 4 carbon atoms. In this preferred embodiment $R^7$ may be hydrogen or alkyl as previously indicated; $R^7$ may also be a salt-forming group (e.g. when $R^5$ is alkylsulfonyl, cycloalkylsulfonyl or arylsulfonyl); this may be a metal (e.g. Na, K or Ca) or ammonium (e.g. $NH_4$ or lower alkyl-substituted ammonium). $R^5$ and $R^7$ may comprise a divalent group such that $NR^5R^7$ together constitute, for instance, a saccharin ring structure,

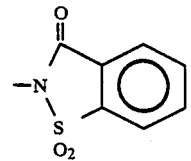

The aryl moiety of the present aryltriazinediones may be a heteroaromatic radical such as a furyl, thienyl, pyridyl, pyrimidyl, oxazolyl, pyrrolyl, isoxazolyl, thiazolyl, or isothiazolyl radical which may carry one or more substituents, for example, halogen and/or alkyl or alkoxy of 1 to 6 (preferably 1 to 4) carbon atoms. Preferably, however, the aryl moiety will be a phenyl radical, particularly a halophenyl radical, more particularly a dihalophenyl radical.

In a preferred embodiment for herbicidal activity, the present compounds will have the formula:

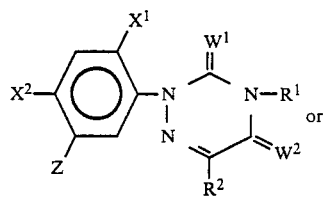

I

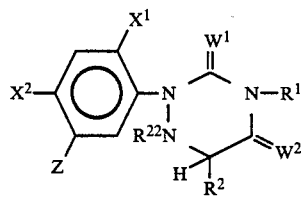

I' in which $X^1$ and $X^2$ are both halogen atoms and Z is as defined above. $X^1$ is preferably chlorine or, especially, fluorine. $X^2$ is preferably chlorine or bromine.

With respect to the triazinedione portion of the molecule, $R^1$ may be alkyl of 1 to 6 (preferably 1 to 4) carbon atoms; haloalkyl of 1 to 56 (preferably 1 to 3) carbon atoms; cyanoalkyl of 1 to 5 (preferably 1 to 3) carbon atoms; alkenyl or alkynyl of 2 to 5 (preferably 3 to 5) carbon atoms; alkoxyalkyl, alkylthioalkyl, alkylsulfinylalkyl, or alkylsulfonylalkyl of 2 to 5 (preferably 2 to 4) carbon atoms; or amino. $R^1$ will frequently and conveniently be a lower alkyl group such as methyl or ethyl, especially methyl. When $R^1$ is haloalkyl, the alkyl radical may be substituted with one or more same or different halogen atoms, preferably the same and preferably fluorine. Typical fluoroalkyl groups include fluoromethyl, difluoromethyl, 2-fluoroethyl, and 3-fluoropropyl. Examples of other $R^1$ substituents include cyanomethyl, amino, 2-propenyl, 2-propynyl, 2-methoxyethyl, methylthiomethyl, methylsulfinylmethyl, and methylsulfonylmethyl. In a preferred embodiment, $R^1$ is methyl or a fluoromethyl having 1 or 2 fluorine atoms, especially methyl. $R^2$ may be hydrogen; halogen, especially fluorine, chlorine, or bromine; alkyl of 1 to 4 carbon atoms, especially methyl; haloalkyl of 1 to 4 carbon atoms, particularly a fluoroalkyl such as trifluoromethyl; cyanoalkyl of 1 to 4 alkyl carbon atoms such as cyanomethyl; alkenyl of 2 to 4 carbon atoms such as 2-propenyl; alkynyl of 2 to 4 carbon atoms such as 2-propynyl; alkoxyalkyl of 2 to 4 carbon atoms, for example, 2-methoxyethyl; amino; hydroxycarbonyl or alkoxycarbonyl of 1 to 4 alkyl carbon atoms. Compounds in which $R^2$ is hydroxycarbonyl, while in themselves or as salts are generally herbicidal at high application rates, are more useful as intermediates (for the corresponding compounds in which $R^2$ is hydrogen) than as herbicides. In a preferred embodiment, $R^2$ is hydrogen or methyl, especially hydrogen.

The groups $W^1$ and $W^2$ are independently selected from oxygen and sulfur. Thus, $W^1$ and $W^2$ may both be oxygen or sulfur, $W^1$ may be oxygen and $W^2$ may be sulfur, or $W^1$ may be sulfur and $W^2$ may be oxygen. In a preferred embodiment $W^1$ and $W^2$ are both oxygen.

A preferred subgenus for high herbicidal activity comprises the compounds of the formula

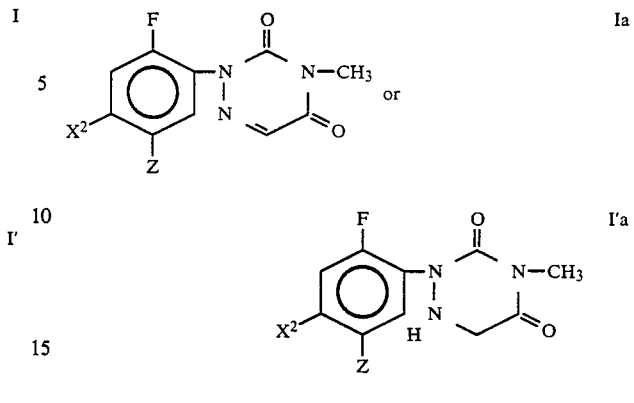

in which $X^2$ is bromine or chlorine and Z is as defined above. Compounds in which the fluorine atom at C-2 of the phenyl ring is replaced by chlorine atom and Z is other than hydrogen are also of particular interest.

It will be understood that any alkyl, alkenyl or alkynyl group herein may be straight chain or branched chain radicals. Thus, 1-methylethyl, 2-methyl-2-propenyl, and 1-methyl-2-propynyl are branched chain examples of alkyl, alkenyl, and alkynyl radicals respectively. Halogen may be fluorine, chlorine, bromine, or iodine. Haloalkyl radicals may have one or more same or different halogen atoms.

Any herbicidal compound of the present invention in which $R^2$ is $CO_2H$ or in which Z is or contains $SO_3H$ or $CO_2H$ or $-SO_2NH-$ may, of course, be converted into a salt such as a sodium, potassium, calcium, ammonium, magnesium, or mono-, di-, or tri($C_1$ or $C_4$ alkyl)ammonium salt which may also be used as an herbicide. Such salts are within the scope of the present invention.

A number of the compounds of the invention may more readily exist in hydrated form rather than as non-hydrated materials. It will be understood that the presence or absence of water of hydration in the compounds is of no concern in determining the metes and bounds of the present invention.

$R^{22}$ is preferably hydrogen, but may be a substituent such as lower alkanoyl (e.g. acetyl); such a substituent may be added by treating the compound in which $R^{22}$ is H with a suitable reagent (e.g. with acetic anhydride in high boiling solvent such as dioxane in the presence of an acetylation catalyst such as N,N-dimethylaminopyridine).

In each aspect of the invention, it is often preferably that any alkyl, alkenyl, alkynyl or alkylene radical have less than 6 carbon atoms.

Representative compounds according to the invention are shown in Table 1 below.

The present compounds may be prepared by methods described in the literature or by methods analogous or similar thereto and within the skill of the art.

Many of the present compounds may be prepared as illustrated in the following chemical equations in which Ar is a substituted or unsubstituted aryl radical, such as

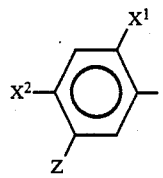

Method A: $R^2$=H or $CO_2H$

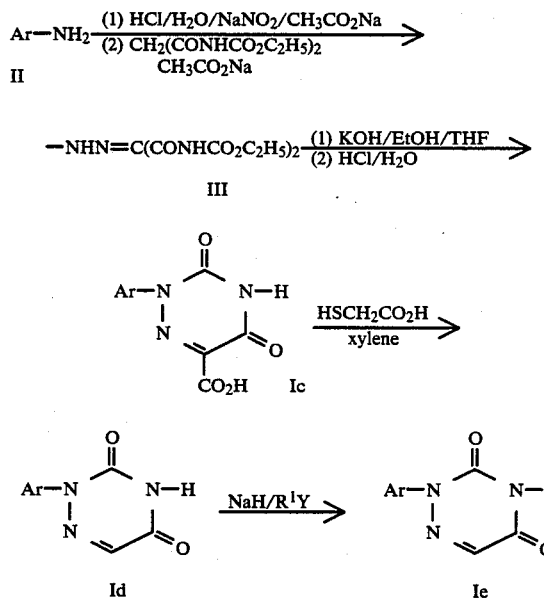

An appropriately substituted or unsubstituted aniline, II, is treated first with aqueous hydrochloric acid, sodium acetate, and sodium nitrite, then with malonyldiurethane and sodium acetate to produce intermediate III. Compound III is cyclized by treatment first with ethanolic potassium hydroxide in tetrahydrofuran, then with aqueous hydrochloric acid to give the triazinedionecarboxylic acid Ic which is decarboxylated in the presence of mercaptoacetic acid and xylene to give the intermediate Compound Id. Treatment of Id with $R^1Y$, in which Y is a suitable leaving group, in the presence of a base gives the N-substituted triazinedione Ie.

Method B: $R^2$=H, alkyl

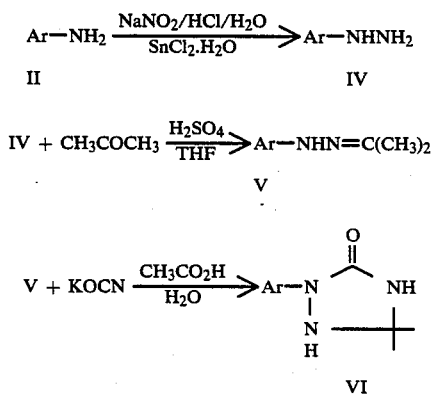

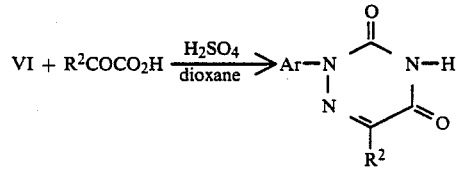

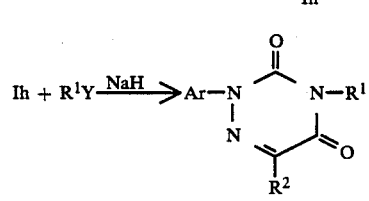

An appropriately substituted or unsubstituted aniline is reacted with sodium nitrite and tin (II) chloride in aqueous hydrochloric acid to produce the corresponding hydrazine, Compound IV, which is converted to hydrazone V by treatment with acetone in sulfuric acid and tetrahydrofuran. Treatment of V with potassium cyanate in aqueous acetic acid gives triazolidinone VI which upon reaction with $R^2COCO_2H$ and sulfuric acid in dioxane produces triazinedione Ih. Reaction of Ih with $R^1Y$ wherein Y is a leaving group gives product Ii.

Method C:
$R^1$=H, alkyl (e.g. methyl), haloalkyl etc. $R^2$=H, alkyl (e.g. methyl) etc. $R^3$=ethyl or other easily split-off group.

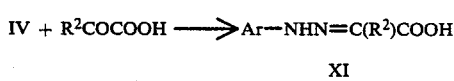

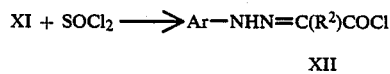

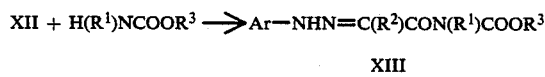

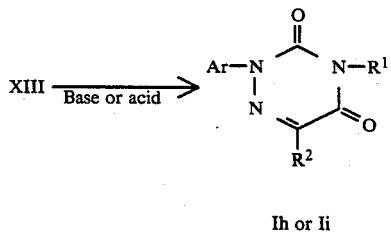

The reaction of an arylhydrazine with glyoxylic acid ($R^2$=H) in dilute hydrochloric acid produces 2-oxoacetic acid arylhydrazone XI. Treatment of this arylhydrazone XI with thionylchloride followed by a urethane produces N-ethoxycarbonyl-2-oxoacetamide arylhydrazone XIII. These first two steps are a modification of a procedure described by HO House, et al *Organic Synthesis*, Vol V, 258–263. Cyclization of arylhydrazone XIII may be accomplished by dissolving XIII in ethanol followed by treatment with dilute potassium hydroxide to produce the corresponding triazine dione Ih or Ii.

In the starting material (compound II), "Ar" may be of the formula

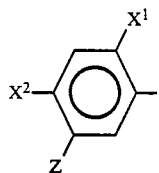

in which the $X^1$, $X^2$ and Z substituents are the same as those in the desired product, as when such a starting material is readily available, either commercially or by preparation, and the substituent Z is stable under the conditions of the process. In some instances the desired Z substituent may be unstable under the conditions used in preparing the starting material II or in converting II into product Ie or Ii. In such cases or where it is otherwise not desirable or convenient to have the desired Z substituent in place at the outset, in Compound II, it may be advantageous to incorporate the desired Z group into the molecule further on in the process, for example, subsequent to the addition of the $R^1$ group.

For example, the products in which Z is $-OR^9$, $-OSO_2R^{10}$, $-OCR^3R^4CO-Q^1R^5$, or $-OR$ (R is other than lower alkyl) may advantageously be prepared from Compound Ie (or Ii) in which Z is lower alkoxy or benzyloxy as illustrated in the following chemical equations:

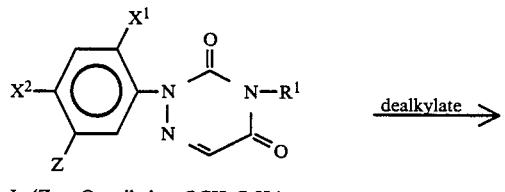

Ie (Z = O—alkyl or $OCH_2C_6H_5$)

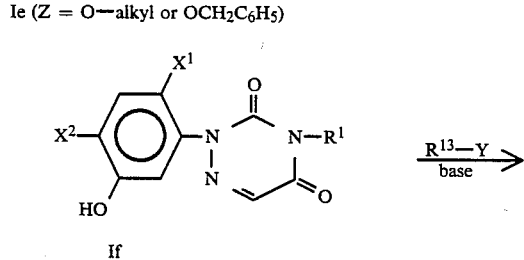

If

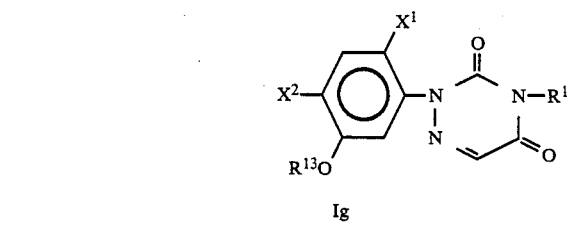

Ig

In the equations above $R^{13}$ represents the appropriate radical $-R^9$, $-SO_2R^{10}$, $-CR^3R^4-CO-Q^1R^5$, or $-R$ and Y represents a leaving group. The phenolic intermediate If is readily prepared from the corresponding compound Ie in which Z is lower alkoxy or benzyloxy by treatment with an acidic reagent such as concentrated sulfuric acid, concentrated hydrobromic acid, or a mixture of hydrobromic and acetic acids to effect dealkylation, or, where Z is benzyloxy, by hydrogenolysis over palladium on charcoal ($H_2/Pd/C/C_2H_5OH$).

Reaction of the 5-hydroxyphenyl intermediate If with the appropriate $R^9-Y$, $R^{10}-SO_2Y$, $Y-CR^3-R^4-CO-Q^1R^5$, or $R-Y$, i.e., $R^{13}-Y$ in the equation above, in the presence of a base gives product Ig.

Similarly, products corresponding to Ie or Ii in which Z is $-SR^{13}$, where $R^{13}$ has the meaning given above, may be prepared by treatment of the corresponding 5-mercaptophenyl compound with $R^{13}-Y$. The 5-mercaptophenyl compound may be prepared from the corresponding compound in which Z is hydrogen (Ie or Ii, Z=H) by the sequence of steps illustrated below:

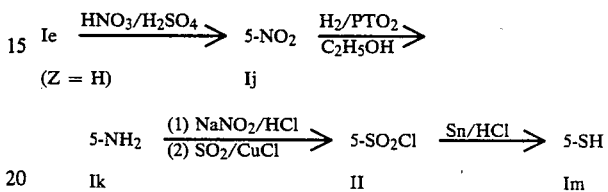

Compound Ie in which Z is hydrogen may be nitrated to give the corresponding 5-nitro compound Ij, which may be reduced to give the corresponding 5-amino compound Ik. Compound Ik may be treated first with $NaNo_2/HCl$, then with $SO_2/CuCl$ to give the 5-chlorosulfonyl compound Il which may be reduced with Sn/HCl to give the corresponding 5-mercapto compound Im.

As with the 5-OH and 5-SH intermediates, the 5-$NH_2$ compound, Ik, is an important intermediate which may be alkylated or acylated to introduce other Z substituents into the molecule. Compounds in which Z is alkoxycarbonylamino, di(alkylcarbonyl)amino, $-NR^7R$, or $-NR^7-CR^3R^4-CO-Q^1R^5$ may be prepared in this manner from the corresponding 5-$NH_2$ compound. An alternative method for introducing certain $-NHR$ or $-NH-CR^3R^4-CO-Q^1R^5$ Z groups is illustrated in the equation below:

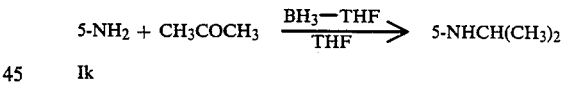

Ik

For example, Compounds 89 (Z=$-NHCH(CH_3)_2$), 206 (Z=$-NH$-cyclohexyl), and 232 (Z=$-NH-CH(CH_3)-CO_2C_2H_5$) shown in Table 1 below were prepared by condensing the corresponding 5-$NH_2$compound with the appropriate ketone in the presence of borane in tetrahydrofuran.

The compound of formula Ie or Ii in which Z is $-NHN=CR^{11}R^{12}$ may also be produced from the corresponding compound in which Z is $-NH_2$ by reacting the 5-$NH_2$ compound with $NaNO_2$ and $SnCl_2$ in aqueous HCl to give the corresponding hydrazine (Ie, Z=$-NHNH_2$), followed by condensation with $R^{11}COR^{12}$.

Example 1 below illustrates a process for making a compound of this invention having a sulfonamide group at the 5-position of the benzene ring by reacting (a) a compound having a phenolic OH group at the 5-position with (b) an N-aryl (or alkyl etc.) sulfonylalkanoic acid amide having a reactive leaving substituent (e.g. Br, Cl, mesylate or tosylate) on the alkane portion of the molecule, e.g.

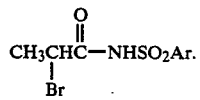

Such a reaction can be carried out in the presence of a base (e.g. in acetone in the presence of sodium or potassium carbonate). Another method for introducing the sulfonamide group is by reacting (a) a compound having an oxypropionic acid substituent at that 5-position with (b) an aryl sulfonylisocyanate.

The compounds in which Z is $-N(R^{21})-SO_2R^{20}$ may be prepared from the amino compounds (Ie or Ii, Z=$-NH_2$) by treatment with $R^{20}SO_2Cl$ to convert the $-NH_2$ group to an $-N(SO_2R^{20})_2$ group. This may then be treated (as with a base such as NaOH) to form the corresponding $-NR^{21}SO_2R^{20}$ group, where $R^{21}$ is a salt-forming group (e.g. Na); this may then be treated with an acid to form the corresponding (acidic) $-NHSO_2R^{20}$ group. Subsequent alkylation (as by treatment with the appropriate alkyl iodide) forms the corresponding

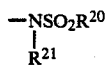

group. When the reaction sequences involves $R^{20}SO_2Cl$ treatment of an intermediate having hydrogen on the 4-nitrogen of the triazine ring, that hydrogen may also be replaced, during such treatment, by $R^{20}SO_2-$ to form an intermediate (such as a compound which has 3 $R^{20}SO_2-$ groups) from which the $R^{20}SO_2-$ group on said 4-nitrogen may be removed readily by the treatment with the base, after which the appropriate $R^2$ group may be substituted on said 4-nitrogen.

The amino compounds (Ie or Ii, Z=$NH_2$) may also be converted into the corresponding compounds in which Z is a halogen atom by treatment with nitrous acid under conditions which give a diazonium salt followed by treatment of the salt with the appropriate halogen reagent, for example, CuCl, CuBr, KI, or $HBF_4$.

The compounds of formula I in which $W^1$ or $W^2$ or both are sulfur may be prepared as follows. Compound Ie or Ii may be treated with one equivalent of $P_2S_5$ in pyridine to give the corresponding compound of formula I in which $W^2$ is sulfur; or Ie or Ii may be treated with at least two equivalents of $P_2S_5$ to produce the dithione derivative (I, $W^1=W^2=S$). Compound I in which $W^1$ is sulfur and $W^2$ is oxygen may be prepared by substituting KSCN for KOCN in Method B above to produce the triazolidinethione corresponding to the triazolidinone VI which may then be carried through the Method B process to give the 1,2,4-triazine-3-thione-5-one product.

The 2-aryl-dihydro-1,2,4-triazine-3,5-diones may be prepared by the selective reduction of the corresponding 1,2,4-triazine-3,5-(2H,4H)-diones, e.g. by using powdered zinc in an aqueous acid medium (e.g. sulfuric acid or more preferably acetic acid) according to the general method set forth in Coll. Czech. Chem. Comm. 39, 3760 (1974). Other methods and descriptions of the hydrogenated compounds are found in Neunhoeffer and Wiley "Chemistry of 1,2,3-Triazines and 1,2,4-Triazines, Tetrazines, and Pentazines" pub. 1978 by Interscience, pages 613–618 and 1006–1033.

In the Examples below (and in the International and parent applications mentioned above) two halogen substituents are present on the "Ar" portion of the molecule before the triazinedione ring is formed; that is, $X^1$ and $X^2$ are halogen in the aryl amine or aryl hydrazine. Instead, in each of the processes illustrated above (and in the process of those Examples) one or both of the halogens may be placed on Ar after the triazinedione ring is formed. For instance, starting with 2-fluoroaniline, the following intermediates may be produced by the sequences illustrated below:

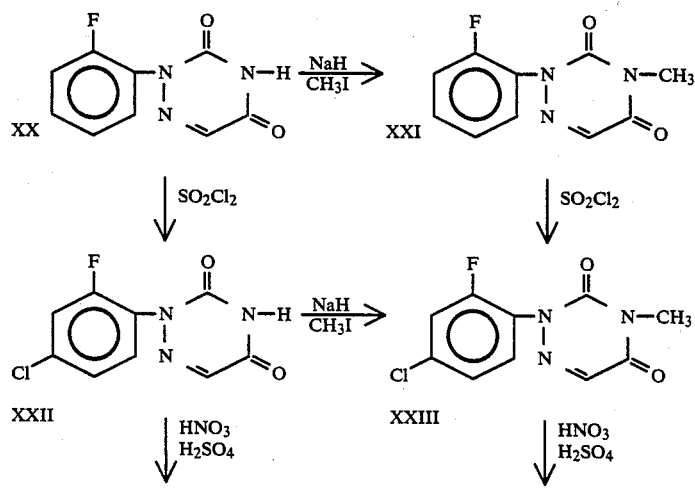

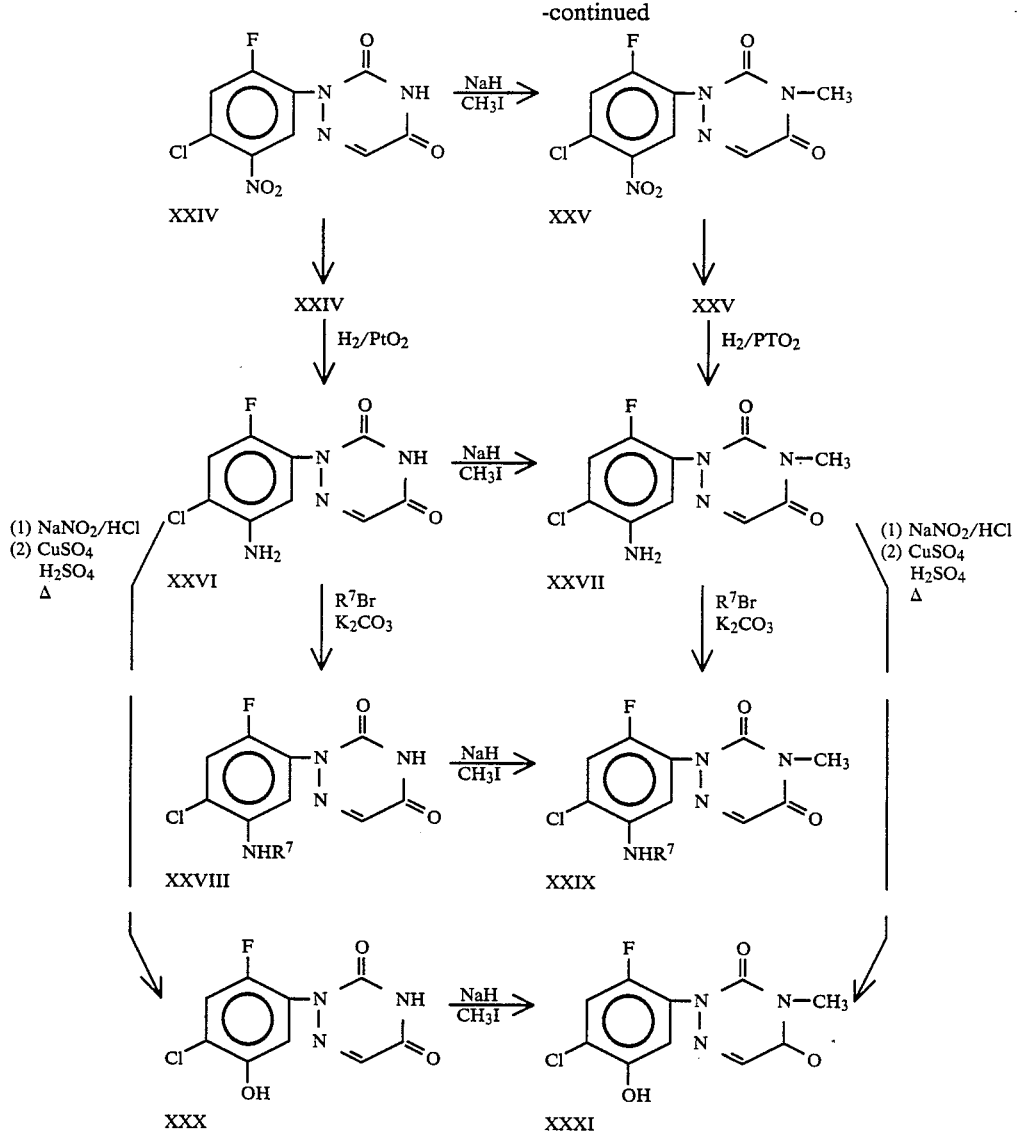

Similar sequences of reactions may be carried out using non-fluorinated aryl amines. For instance, one sequence of reactions, starting with 3-nitroaniline, involves the following intermediates:
1-(5-nitrophenyl)-1,2,4-triazine-3,5-dione, then
1-(5-nitrophenyl)-4-methyl-1,2,4-triazine-3,5-dione, then
1-(5-aminophenyl)-4-methyl-1,2,4-triazine-3,5-dione,
  then the corresponding compound having the desired Z substituent (or a precursor thereof) at a meta-position on the benzene ring such as
1-[5-(N-ethylsulfonyl)aminophenyl]-4-methyl-1,2,4-triazine-3,5-dione, followed by halogenation to place, for instance, two chloro (or bromo) substituents at the 2- and 4-positions of the benzene ring.

Variations in the sequence in which the reactions are carried out will produce other intermediates such as:
1-(2-chloro-5-nitrophenyl)-4-methyl-1,2,4-triazine-3,5-dione, which may be converted to the corresponding 2-fluoro-5-nitrophenyl compound by appropriate treatment with KF to replace the 2-chloro substituent by a 2-fluoro substituent;
also, 1-(2-fluorophenyl)-1,2,4-triazine-3,5-dione, which may be converted to
1-(2-fluorophenyl)-4-methyl-1,2,4-triazine-3,5-dione, which may then be chlorinated, as by appropriate treatment with SO$_2$Cl$_2$, to the corresponding 2-fluoro-4-chlorophenyl compound.

Another sequence involves formation of:
2-fluoro-4-nitrophenylhydrazine, then
1-(2-fluoro-4-nitrophenyl)-1,2,4-triazine-3,5-dione, then
1(-2-fluoro-4-nitrophenyl)-4-methyl-1,2,4-triazine-3,5-dione, then
1-(2-fluoro-4-aminophenyl)-4-methyl-1,2,4-triazine-3,5-dione, followed by treatment to replace the amino group by a chlorine (as by treatment with NaNO$_2$/HCl and then CuCl).

Another starting material may be, for instance, 4-fluorophenyl methyl ketone, which may be converted to the desired product through sequences forming intermediates such as those illustrated below, in which the acetyl group in converted to a hydroxyl group by a Baeyer-Villiger reaction (by the action of a peracid):

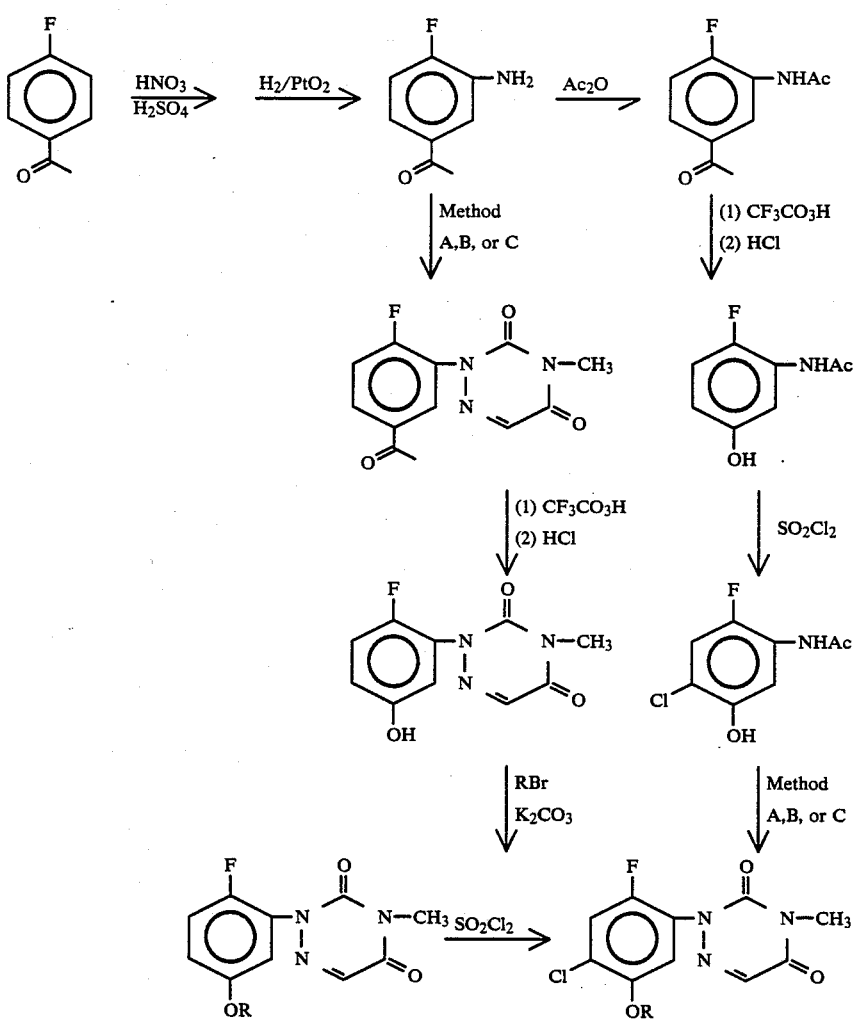

Representative compounds of the invention are shown in Tables 1 and A-1. Characterizing data and herbicidal data for many of the compounds, as well as illustrations of the methods of preparation, are found in the above-mentioned published International (PCT) application and U.S. patent applications. Additional characterizing and herbicidal data and illustrative methods are given in the Examples and Tables 2, 2A, 3 and 4 below. All temperatures are in degrees Celsius, and all pressures are in mm Hg unless otherwise noted.

EXAMPLE 1

N-(4-chlorophenylsulfonyl)-2-[2-chloro-4-fluoro-5-(4-methyl-3,5-dioxo-2H,4H-1,2,4-triazin-2-yl)-phenoxy]-propionamide To a stirred solution of 0.62 g (0.0023 mole) of 1-(4-chloro-2-fluoro-5-hydroxyphenyl)-4-methyl-1,2,4-triazine-3,5-(2H,4H)-dione (compound 30) and 0.75 g (0.0023 mole) of N-(4-chlorophenylsulfonyl)-2-bromopropionamide in 25 mL of acetone was added 0.35 g (0.0023 mole) of potassium carbonate. After complete addition the mixture was heated at reflux for approximately 18 hours. The mixture was cooled and poured into ice water. This mixture was extracted with ethyl acetate. The extract was dried over anhydrous magnesium sulfate and filtered. The filtrate was evaporated under reduced pressure leaving a solid residue. This residue was subjected to column chromatography on silica gel, eluted with n-heptane:ethylacetate (1:1), to yield 0.53 g of a semisolid. This foam was dissolved in ethylacetate, and the solution was washed with water. The washed solution was dried over anhydrous magnesium sulfate and filtered. The filtrate was evaporated under reduced pressure to yield 0.33 g of N-(4-chlorophenylsulfonyl)-2-[2-chloro-4-fluoro-5-(4-methyl-3,5-dioxo-2H,4H-1,2,4-triazin-2-yl)phenoxy]propionamide as a solid, (mp 97° C., dec.) compound 209 in the Tables.

The nmr and ir spectra were consistent with the proposed structure.

To obtain compound 269 of Table 1 N-(3-methyl-4-methoxyphenylsulfonyl)-2bromopropionamide is used in place of the N-(4-chlorophenylsulfonyl)-2-bromopropionamide.

EXAMPLE 2

Synthesis of 2-(5-Amino-4-chloro-2-fluorophenyl)-4-methyl-1,2,4-triazine-3,5(2H,4H)-dione as an intermediate Step A Synthesis of 2-fluoroacetanilide as an intermediate To a stirred suspension of 1800 g (16.2 moles) of 2-fluoroaniline n 2200 mL of water was added dropwise 1817 g (17.8 moles) of acetic anhydride. The complete addition required 90 minutes during which time the reaction mixture temperature rose to 35°–40° C. Upon completion of addition the reaction mixture was stirred for two hours while it cooled to ambient temperature. The reaction mixture was filtered to collect, when dried, 1942.2 g of 2-fluoroacetanilide.

The nmr spectrum was consistent with the proposed structure.

Step B Synthesis of 4-chloro-2-fluoroacetanilide as an intermediate

To a stirred solution of 1233 g (8.06 moles) of 2-fluoroacetanilide in 1440 mL of dioxane was slowly added 1186 g (8.79 moles) of sulfuryl chloride. During the 4.5 hour addition time the reaction mixture temperature was controlled with an ice-water bath. Upon completion of addition an additional 200 mL of dioxane was added to the reaction mixture and it was allowed to stir at ambient temperature for 21 hours. Water, 150 mL, was added to the reaction mixture; which was then filtered to collect a solid. The solid, as determined by gas chromatographic (GC) analysis, was 100% 4-chloro-2-fluoroacetanilide. The filtrate was poured into 3000 mL of ice-water to yield a second crop of product. The crops were combined to yield a total of 1204 g of 4-chloro-2-fluoroacetanilide that was 99% pure by GC analysis.

Step C Synthesis of 4-chloro-2-fluoroaniline as an intermediate

Under a nitrogen atmosphere, a suspension of 718 g (3.8 moles) of 4-chloro-2-fluoroacetanilide in 2653 mL of ethanol was stirred as a solution of 304 g (7.6 moles) of sodium hydroxide in 1075 mL of water was added. Upon completion of addition the reaction mixture was warmed to 80° C. during a 2.3 hour period. The reaction mixture was cooled to ambient temperature and concentrated under reduced pressure to a volume of approximately 2000 mL. The concentrate was dissolved in 2000 mL of ethyl acetate and washed with 500 mL of water. The organic layer was concentrated under reduced pressure to a residual oil. The oil was filtered to remove a solid, then distilled under reduced pressure to yield 329 g of 4-chloro-2-fluoroaniline; b.p. 93°–100° C./16–20 mm.

The nmr and the ir spectra were consistent with the proposed structure.

Step D Synthesis of N,N'-carboethoxy-2-ketomalonodiamide 4-chloro-2-fluorophenylhydrazone as an intermediate A stirred solution of 35.0 g (0.24 mole) of 4-chloro-2-fluoroaniline and 41 mL of concentrated hydrochloric acid in 750 mL of water was cooled to 0° C. and a solution of 16.6 g (0.24 mole) of sodium nitrite in 50 mL of water was added dropwise using a dropping funnel with a tip that extended below the surface of the reaction mixture. In a separate vessel a stirred solution of 59.0 g (0.24 mole) of malonyl diurethane and 98.0 g (1.2 moles) of sodium acetate in 2200 mL of water was cooled to 10° C. The cold diazonium solution prepared above was added to this in one portion. Upon completion of addition the reaction mixture stirred for two hours during which time a solid formed. The solid was collected by filtration to yield 96.7 g of N,N'-carboethoxy-2-ketomalonodiamide 4-chloro-2-fluorophenylhydrazone.

Step E Synthesis of 2-(4-chloro-2-fluorophenyl)-1,2,4-triazine-3,5(2H,4H)-dione-6-carboxylic acid as an intermediate To a stirred suspension of 96.7 g (0.24 mole) of N,N'-carboethoxy-2-ketomalonodiamide 4-chloro-2-fluorophenylhydrazone in 900 mL of ethanol and 2000 mL of tetrahydrofuran was added a solution of 26.9 g (0.48 mole) of 85% potassium hydroxide in 150 mL of after. The resultant thick slurry was stirred for 45 minutes, then the volatile organic solvents were removed under reduced pressure. The aqueous residue mixture was filtered to remove a solid. The filtrate was washed with ethyl acetate then acidified with concentrated hydrochloric acid. The mixture was extracted with ethyl acetate and the extract dried with magnesium sulfate. The mixture was filtered and the filtrate concentrated under reduced pressure to yield 59.0 g of 2-(4-chloro-2-fluorophenyl-1,2,4-triazine-3,5(2H,4H)-dione-6-carboxylic acid as a solid.

The nmr spectrum was consistent with the proposed structure.

Step F Synthesis of 2-(4-chloro-2-fluorophenyl-1,2,4-triazine-3,5(2H,4H)-dione as an intermediate A solution of 59.0 g (0.207 mole) of 2-(4-chloro-4-fluorophenyl)-1,2,4-triazine-3,5(2H,4H)-dione-6carboxylic acid in 30° C. for three hours. The reaction mixture was cooled to ambient temperature and the resultant solid triturated with heptane-ethyl acetate. The solid, soluble in ethylacetate, was dissolved in ethyl acetate and washed with four 400 mL portions of water. The organic layer was dried with sodium sulfate and filtered. The filtrate was concentrated under reduced pressure to yield 28.0 g of 2-(4-chloro-2-fluorophenyl)-1,2,4-triazine-3,5(2H,4H)-dione as a solid.

Step G Synthesis of 2-(4-chloro-2-fluorophenyl)-4-methyl-1,2,4-triazine-3,5(2H,4H)-dione as an intermediate Sodium hydride, 3.4 g (0.14 mole—60% in mineral oil) as stirred with heptane. The heptane was decanted and 100 mL of dimethylformamide was added to the sodium hydride. A solution of 28.0 g (0.116 mole) of 2-(4-chloro-2-fluorophenyl)-1,2,4-triazine-3,5-(2H,4H)-dione in 150 mL of dimethylformamide was added dropwise to the stirred suspension of sodium hydride. Upon completion of addition the reaction mixture was stirred at ambient temperature for 30 minutes, then 19.9 g (0.14 mole) of methyl iodide was added dropwise. Upon completion of addition the reaction mixture was stirred at ambient temperature for two hours. The reaction mixture was poured into ice-water. The mixture was extracted with ethyl acetate and the combined extracts dried with sodium sulfate. The mixture was filtered and the filtrate concentrated under reduced pressure to yield 25.0 g of 2-(4-chloro-2-fluorophenyl)-4-methyl-1,2,4-triazine-03,5(2H,4H)-dione as a solid.

The nmr spectrum was consistent with the proposed structure.

Step H Synthesis of 2-(4-chloro-2-fluoro-5-nitrophenyl)-4-methyl-1,2,4-triazine-3,5(2H,4H)-dione as an intermediate To a stirred solution of 24.7 g (0.097 mole) of 2-(4-chloro-2-fluorophenyl)-4-methyl-1,2,4-triazine-3,5(2H,4H)-dione in 30 mL of concentrated sulfuric acid was added dropwise a mixture of 70 mL of concentrated sulfuric acid and 100 mL of fuming nitric acid. The reaction mixture temperature was kept below 40° C. during the addition. Upon completion of addition the reaction mixture was stirred at ambient temperature for four hours. The reaction mixture was poured into ice-water and the mixture extracted with ethyl acetate. The combined extracts were dried with sodium sulfate and filtered. The filtrate was concentrated under reduced pressure to yield a solid. The solid was triturated with diethyl ether and collected by filtration to yield 20.6 g of 2-(4-chloro-2-fluoro-5-nitrophenyl)-4-methyl-1,2,4-triazine-3,5(2H,4H)-dione.

The nmr spectrum was consistent with the proposed structure.

Step I Synthesis of
2-(5-amino-4-chloro-2-fluorophenyl)-4-methyl-1,2,4-triazine-3,5(2H,4H)-dione as an intermediate A solution of 18.0 g (0.060 mole) of 2-(4-chloro-2-fluoro-5-nitrophenyl)-4-methyl-1,2,4-triazine-3,5-(2H,4H)dione in 200 mL of ethanol was placed in a 500 mL Parr hydrogenation bottle with 0.5 g of platinum oxide. The bottle was placed in a Parr hydrogenator and the reaction mixture hydrogenated. Upon complete hydrogenation the reaction mixture was filtered to remove the catalyst. The filtrate was concentrated under reduced pressure to a residual oil. The oil was purified using column chromatography on silica gel. Elution was accomplished with 1:1—ethyl acetate: heptane. The appropriate fractions were combined and concentrated under reduced pressure to yield 13.0 g of 2-(5-amino-4-chloro-2-fluorophenyl)-4-methyl-1,2,4-triazine-3,5(2H,4H)-dione; m.p. 150–152° C.

The nmr spectrum was consistent with the proposed structure.

EXAMPLE 3

Synthesis of
2-[4-chloro-2-fluoro-5-[bis(N-methylsulfonyl)amino]-phenyl]-4methyl-1,2,4-triazine-3,5(2H,4H)-dione To a stirred solution of 1.0 g (0.004 mole) of 2-(5-amino-4-chloro-2-fluorophenyl)-4-methyl-1,2,4-triazine-3,5(2H,4H)-dione (prepared as in Example 2) and 0.74 g (0.007 mole) of triethylamine in 20 mL of methylene chloride was added 0.9 g (0.007 mole) of methanesulfonyl chloride. Upon completion of addition the reaction mixture stirred at ambient temperature for 18 hours. The reaction mixture was subjected to column chromatography on silica gel using methylene chloride, then 1:19 acetone:methylene chloride as eluents. The appropriate fractions were combined and concentrated under reduced pressure to yield 2.0 g of impure product. The impure material was subjected to a second column chromatography on silica gel using methylene chloride as an eluent. The appropriate fractions were combined and concentrated under reduced pressure to yield 1.1 g of 2-[4-chloro-2-fluoro-5-[bis(N-methylsulfonyl)amino]phenyl]-4-methyl-1,2,4-triazine-3,5-(2H,4H-dione (m.p. 211–213° C.), compound 257 of Table 1.

The nmr spectrum was consistent with the proposed structure.

EXAMPLE 4

Synthesis of
2-[4-chloro-2-fluoro-5-(N-methylsulfonylamino)-phenyl]-4-methyl-1,2,4-triazine-3,5(2H,4H)-dione To a stirred solution of 0.75 g (0.002 mole) of 2-[4-chloro-2-fluoro-5-[bis(N-methylsulfonyl)amino]-phenyl]-4-methyl-1,2,4-triazine-3,5(2H,4H)-dione (prepared as in Example 3) in 40 mL of methanol was added a solution of 0.14 g (0.004 mole) of sodium hydroxide in 3 mL of water. Upon completion of addition the reaction mixture was stirred at ambient temperature for 20 minutes then 40 mL of water was added. The mixture was made acidic with concentrated hydrochloric acid and concentrated under reduced pressure to remove methanol. The concentrate was extracted with ethyl acetate and the combined extracts were dried with sodium sulfate. The mixture was filtered and the filtrate concentrated under reduced pressure to a residue. The residue was purified by column chromatography on silica gel using 1:1—ethyl acetate:heptane as the eluent. The appropriate fractions were combined and concentrated under reduced pressure to yield 0.42 g of 2-[4-chloro-2-fluoro-5-(N-methylsulfonylamino)phenyl]-4-methyl-1,2,4-triazine-3,5(2H,4H)-dione (m.p. 70° C., dec.), compound 258 of Table 1.

The nmr spectrum was consistent with the proposed structure.

EXAMPLE 5

2-[4-chloro-2-fluoro-5-(2-propynyloxy)phenyl]-1,6-dihydro-4-methyl-1,2,4-triazine-3,5(2H,4H)-dione A solution of 1.6 g (0.0052 mole) of 2-(4-chloro-2-fluoro-5-(2-propynyloxy)phenyl]-4-methyl-1,2,4-triazine-3.5(2H,4H)-dione (compound 21) dissolved in 5 mL of glacial acetic acid was added dropwise to a stirred suspension of 1.5 g (0.023 mole) of zinc dust in 10 mL of glacial acetic acid and 5 mL of water. After complete addition the mixture was heated at 60° C. for 1.5 hours. The mixture was filtered and the filtrate was partitioned between 50 mL of water and 50 mL of diethyl ether. The organic phase was washed first with water followed by a saturated aqueous sodium bicarbonate solution. The washed organic phase was dried over anhydrous magnesium sulfate and filtered. The filtrate was evaporated under reduced pressure to yield 1.2 g of 2-[4-chloro-2-fluoro-5-(2-propynyloxy)phenyl]-1,6-dihydro-4-methyl-1,2,4-triazine-3,5(2H,4H)-dione as an oil, compound A-3 of Table A-1.

The nmr spectrum was consistent with the proposed structure.

EXAMPLE 6

2-(2,4-Dichlorophenyl)-1,2,4-triazine-3,5(2H,4H)-dione (A compound which may be nitrated introduce a 5-NO$_2$ group on the benzene ring, as indicated above)

Step A 2-Oxoacetic acid 2,4-dichlorophenylhydrazone

In a manner similar to that disclosed by HO House, et al (*Organic Synthesis*, Vol V, 258–263) the reaction of 3.4 g (0.046 mole) of glyoxylic acid in 40 mL of 2.5 N hydrochloric acid and 60 mL of water with a solution of 9.8 g (0.046 mole) of 2,4-dichlorophenylhydrazine hydrochloride in 30 mL of water produced 7.4 g of 2-oxoacetic acid 2,4-dichlorophenylhydrazone as a solid (m.p. 160° C., dec.).

The nmr spectrum was consistent with the proposed structure.

Step B
2-(2,4-Dichlorophenyl)-1,2,4-triazine-3,5(2H,4H)-dione

To a stirred mixture of 5.9 g (0.025 mole) of 2-oxoacetic acid 2,4-dichlorophenylhydrazone in 100 mL of toluene was added 6.0 g (0.051 mole) of thionyl chloride. The reaction mixture was heated at reflux for 10 minutes resulting in a clear solution. This solution was cooled and the solvent was removed by evaporation under reduced pressure leaving a solid residue. This solid was dissolved in 100 mL of fresh toluene to which 2.7 g (0.030 mole) of urethane was added. The resultant mixture was heated at reflux for three hours, removing about 50 mL of solvent by means of a Dean-Stark trap. The reaction mixture was cooled and the solvent removed by evaporation under reduced pressure leaving a yellow residue. This residue was dissolved in 50 mL of ethanol to which was added 50 mL of an aqueous 10% potassium hydroxide solution. The resultant mixture was heated on a steam bath for 15 minutes. The mixture was allowed to cool and was diluted with additional water. The dilute aqueous mixture was washed with diethyl ether. The aqueous phase was acidified with concentrated hydrochloric acid and the acidic mixture was extracted with ethyl acetate. The extract was dried over anhydrous magnesium and sulfate and filtered. The filtrate was evaporated under reduced pressure leaving a residue. This residue was dissolved in about 20 mL of ethyl acetate and filtered through a pad of silica gel. The filtrate was evaporated under reduced pressure leaving a solid. Purification of this solid by recrystallization from ethyl acetate/n-heptane yielded 3.0 g of 2-(2,4-dichlorophenyl)-1,2,4-triazine-3,5(2H,4H)-dione.

The nmr spectrum was consistent with the proposed structure.

Other compounds of the invention may be prepared by the methods exemplified above or by methods within the skill of the art.

HERBICIDAL ACTIVITY

The plant test species used in demonstrating the herbicidal activity of compounds of this invention include cotton (*Gossypium hirsutum* var. Stoneville), soybean (*Glycine max* var. Williams) filed corn (*Zea mays* var. Agway 595S), wheat (*Triticum aestivium* var. Prodax), rice (*Oryza sativa* var. Labelle), field bindweed (*Convolvulus arvensis*), morningglory (*Ipomea lacunosa* or *Ipomea Ipomea hederacea*), velvetleaf (*Abutilon theophrasti*), barnyardgrass (*Echinochloa crus galli*), green foxtale (*Setaria viridis*), and johnsongrass (*Sorghum halepense*), yellow nutsedge (*Cyperus esculentus*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

For testing the effectiveness with paddy rice, plastic flats (35.5 cm×6.4 cm×12.7 cm) were lined with plastic film and filled to a depth of about 3.0 cm with steam-sterilized sandy loam soil. The soil was leveled and seeds of rice (*Oryza sativa* var. Mars or Labelle) and flatsedge rice (*Cyperus iria*), a weed, were planted and topped with about 0.5 cm of sandy loam soil. The flat was placed in the greenhouse and watered for 7 to 8 days. Hemp Sesbania (*Sesbania exaltata*), barnyardgrass (*Echinochloa Crus-galli*), and green sprangletop (*Leptochloa imbricata*) were planted in the remaining space in the flat. The flats were again placed in the greenhouse and watered for another seven or eight days so that all the seeds sprouted. The flats were then drenched with water to a level of 2 to 3 cm above the soil. Directly after their drenching the candidate herbicides were applied as aqueous-acetone solutions at a range of rates equivalent to 0.5 kg/ha and submultiples thereof, i.e. 0.25 kg/ha, 0.125 kg/ha, and so on. The appropriate amount of test solution was pipetted into the water layer above the soil, distributing the solution evenly. After application of the test solution the drenched flats were placed in the greenhouse and watered regularly to keep the soil covered with water. After 14 days phytotoxicity data were recorded and expressed as percent control as compared to a flat which had not been treated with herbicide. The temperature of the greenhouse was about 30° C.

Herbicidal data at selected application rates are given for various compounds of the invention in Table 3 and Table 4 below. The test compounds are identified therein by numbers which correspond to those in Table 1.

In Tables 3 and 4 below:
"kg/ha" is kilograms per hectare, and
"% C" is percent control.

It is clear from the data that the generic class of aryl-triazinediones and sulfur analogs thereof described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal application, the active compounds as above defined are formulated into herbicidal compositions, by admixture, in herbicidally effective amounts, with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient y weight of the herbicidal composition.

Typical wetting, dispersing, or emulsifying agents used in agricultural formulations include, for example, the alkyl and alkylaryl sulfonates and sulfates and their sodium salts, polyhydric alcohols, and other types of surface active agents, many of which are available in commerce. The surface active agent, when used, normally comprises 1% to 15% by weight of the herbicidal composition.

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. The amount may, for example, be in the range of about 4 to 250 g/ha such as 7 or 15 to 65 g/ha.

The active herbicidal compounds of this invention may be used in combination with other herbicides, e.g. they may be mixed with,m say, an equal or larger amount of a known herbicide such as chloroacetanilide herbicides such as 2-chloro-N-(2,6-diethylphenyl)-N-(methoxymethyl)acetamide (alachlor), 2-chloro-N(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrizine), and 2-[4-chloro-6-(ethylamino)-1,3,5-triazin-2-yl]amino -2-methylpropanenitrile (cyanazine); dinitrolaniline herbicides such as 2,6-dinitro-N,N-dipropyl-4-(trifluoromethyl)benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron).

It is apparent that various modifications may be made in the formulation and application of the compounds of this invention without departing from the inventive concepts herein as defined in the claims.

TABLE 1
Representative Compounds

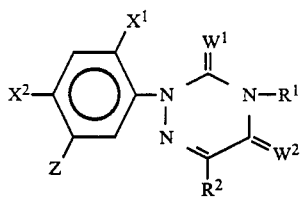

(Except where indicated otherwise, $W^1 = W^2 =$ oxygen).

| Compound Number | $X^1$ | $X^2$ | Z | $R^1$ | $R^2$ |
|---|---|---|---|---|---|
| 1 | H | H | H | $CH_3$ | H |
| 2 | F | H | H | $CH_3$ | H |
| 3 | H | Cl | H | $CH_2CH=CH_2$ | H |
| 4 | Cl | Cl | H | H | $CH_3$ |
| 5 | Cl | Cl | H | $CH_3$ | $CH_3$ |
| 6 | F | Cl | H | H | H |
| 7 | F | Cl | H | $CH_3$ | H |
| 8[4] | Cl | Cl | H | $CH_3$ | H |
| 9 | Cl | Cl | OH | $CH_3$ | H |
| 10 | Cl | Cl | $OCH(CH_3)_2$ | H | $CH_3$ |
| 11 | Cl | Cl | $OCH(CH_3)_2$ | H | $CO_2H$ |
| 12 | Cl | Cl | $OCH(CH_3)_2$ | $CH_3$ | H |
| 13 | Cl | Cl | $OCH(CH_3)_2$ | $CH_3$ | $CH_3$ |
| 14 | Cl | Cl | $OCH(CH_3)_2$ | $CH_3$ | $CO_2H$ |
| 15 | Cl | Cl | $OCH(CH_3)_2$ | $CH_2CH=CH_2$ | H |
| 16 | Cl | Cl | $OCH(CH_3)_2$ | $CH_2CH=CH_2$ | $CH_3$ |
| 17 | F | Cl | $OCH(CH_3)_2$ | H | H |
| 18 | F | Cl | $OCH(CH_3)_2$ | $CH_3$ | H |
| 19 | F | Cl | $OCH(CH_3)_2$ | $CH_2CH=CH_2$ | H |
| 20 | Cl | Cl | $OCH_2C\equiv CH$ | $CH_3$ | H |
| 21 | F | Cl | $OCH_2C\equiv CH$ | $CH_3$ | H |
| 22 | Cl | Cl | $OCH_2CO_2C_2H_5$ | $CH_3$ | H |
| 23 | Cl | Cl | $OSO_2CH_3$ | $CH_3$ | H |
| 24[1] | F | Cl | $OCH_2C\equiv CH$ | $CH_3$ | H |
| 25 | Cl | Cl | $OCH(CH_3)_2$ | $CH_2C\equiv CH$ | H |
| 26 | Cl | Cl | $OCH(CH_3)_2$ | $CH_2CH_2F$ | H |
| 27 | Cl | Cl | $OCH(CH_3)CO_2C_2H_5$ | $CH_3$ | H |
| 28 | Cl | Cl | $OCH_2CN$ | $CH_3$ | H |
| 29 | Cl | Cl | $OCH(CH_3)_2$ | $C_2H_5$ | H |
| 30 | F | Cl | OH | $CH_3$ | H |
| 31 | H | Cl | H | H | $CO_2H$ |
| 32 | H | Cl | $OCH_3$ | H | $CO_2H$ |
| 33 | H | Cl | H | H | H |
| 34 | H | $CH_3$ | H | H | H |
| 35 | H | $CH_3$ | H | $CH_3$ | H |
| 36 | H | Cl | H | $CH_3$ | H |
| 37 | H | Cl | $OCH_3$ | H | H |
| 38 | H | $OCH_3$ | H | H | H |
| 39 | H | Cl | $OCH_3$ | $CH_3$ | H |
| 40 | H | $OCH_3$ | H | $CH_3$ | H |
| 41 | F | Cl | $OCH(CH_3)_2$ | $CH_2F$ | H |
| 42 | F | Cl | $OCH(CH_3)CO_2CH_3$ | $CH_3$ | H |
| 43 | F | Cl | $OCH_2CO_2C_2H_5$ | $CH_3$ | H |
| 44 | F | Cl | $OCH_2C\equiv CH$ | $CH_2F$ | H |
| 45 | F | Cl | $OCH(CH_3)_2$ | $CH_2CN$ | H |
| 46 | F | Cl | $NO_2$ | $CH_3$ | H |
| 47 | F | Cl | $NH_2$ | $CH_3$ | H |
| 48 | F | Cl | $OCH_2C\equiv CBr$ | $CH_3$ | H |
| 49 | F | Cl | $OCH_2CONH_2$ | $CH_3$ | H |
| 50 | F | Cl | $OCH(CH_3)_2$ | $CH_2(CH_2)_2F$ | H |
| 51 | Cl | Cl | $OCH(CH_3)_2$ | H | H |
| 52 | F | Cl | $OCH_2C\equiv Cl$ | $CH_3$ | H |
| 53 | F | Br | $OCH(CH_3)_2$ | $CH_3$ | H |
| 54 | F | H | $OCH(CH_3)_2$ | $CH_3$ | H |
| 55 | F | $CH_3$ | $OCH(CH_3)_2$ | $CH_3$ | H |
| 56 | F | $CF_3$ | $OCH_2C\equiv CH$ | $CH_3$ | H |
| 57 | F | $OC_6H_5$ | $OCH_2C\equiv CH$ | $CH_3$ | H |
| 58 | F | $OCH_2C_6H_5$ | $OCH(CH_3)_2$ | $CH_3$ | H |
| 59 | F | Cl | $NHCH_3$ | $CH_3$ | H |
| 60 | F | Cl | $N(CH_3)_2$ | $CH_3$ | H |
| 61[1] | F | Cl | $OSO_2CH_3$ | $CH_3$ | H |
| 62 | F | Cl | $CO_2H$ | $CH_3$ | H |
| 63 | F | Cl | $CO_2CH_3$ | $CH_3$ | H |
| 64 | F | Cl | $CO_2C_2H_5$ | $CH_3$ | H |
| 65 | F | Cl | $CO-SCH_3$ | $CH_3$ | H |

TABLE 1-continued

Representative Compounds

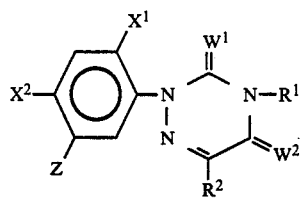

(Except where indicated otherwise, $W^1 = W^2 =$ oxygen).

| Compound Number | $X^1$ | $X^2$ | Z | $R^1$ | $R^2$ |
|---|---|---|---|---|---|
| 66 | F | Cl | $CO_2CH_2CH_2OCH_3$ | $CH_3$ | H |
| 67 | F | Cl | $CONH_2$ | $CH_3$ | H |
| 68 | F | Cl | $CONHCH_3$ | $CH_3$ | H |
| 69 | F | Cl | $CON(CH_3)_2$ | $CH_3$ | H |
| 70 | F | Cl | $CONHCH_2CH_2OCH_3$ | $CH_3$ | H |
| 71 | F | Cl | $CON(CH_3)CH_2CH_2OCH_3$ | $CH_3$ | H |
| 72 | F | Cl | $OCH(CH_3)_2$ | $CH_2C{\equiv}CH$ | H |
| 73 | F | Cl | $OCH(CH_3)_2$ | $NH_2$ | H |
| 74 | F | Cl | $OCH_2C{\equiv}CH$ | $CH_2CN$ | H |
| 75 | F | Cl | NHCH(CH$_3$)CONHCH(C$_2$H$_5$)CH$_3$ | $CH_3$ | H |
| 76 | F | Cl | OCH(CH$_3$)CONHCH(C$_2$H$_5$)CH$_3$ | $CH_3$ | H |
| 77 | F | Cl | $CH_3$ | $CH_3$ | H |
| 78 | F | Cl | O-cyclopentyl | $CH_3$ | H |
| 79 | F | Cl | $CF_3$ | $CH_3$ | H |
| 80 | F | Cl | SH | $CH_3$ | H |
| 81 | F | Cl | $SO_3H$ | $CH_3$ | H |
| 82 | F | Cl | $SCH_3$ | $CH_3$ | H |
| 83 | F | Cl | $SOCH_3$ | $CH_3$ | H |
| 84 | F | Cl | $SO_2CH_3$ | $CH_3$ | H |
| 85 | F | Cl | $SCH(CH_3)_2$ | $CH_3$ | H |
| 86 | F | Cl | $SCH_2C{\equiv}CH$ | $CH_3$ | H |
| 87 | F | Br | $NHCH(CH_3)CO_2C_2H_5$ | $CH_3$ | H |
| 88 | F | Cl | $NHCH(CH_3)CONHCH_3$ | $CH_3$ | H |
| 89 | F | Cl | $NHCH(CH_3)_2$ | $CH_3$ | H |
| 90 | F | Cl | $NHCH_2C{\equiv}CH$ | $CH_3$ | H |
| 91 | F | Cl | NH-cyclopentyl | $CH_3$ | H |
| 92 | F | Cl | $NHCOCH_3$ | $CH_3$ | H |
| 93 | F | Cl | $NHCO_2CH_3$ | $CH_3$ | H |
| 94 | F | Cl | O-cyclohexyl | $CH_3$ | H |
| 95 | F | Cl | $OCF_2H$ | $CH_3$ | H |
| 96 | F | Cl | $OCH_2OCH_3$ | $CH_3$ | H |
| 97 | F | Cl | O-(tetrahydrofuranyl) | $CH_3$ | H |

TABLE 1-continued
Representative Compounds

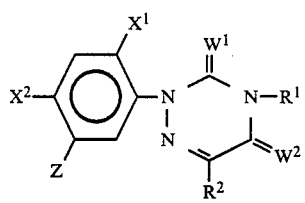

(Except where indicated otherwise, $W^1 = W^2 =$ oxygen).

| Compound Number | $X^1$ | $X^2$ | Z | $R^1$ | $R^2$ |
|---|---|---|---|---|---|
| 98 | F | Cl | OCH₂-(tetrahydrofuran-2-yl) | CH₃ | H |
| 99 | F | Cl | OCH₂-(tetrahydropyran-2-yl) | CH₃ | H |
| 100 | F | Cl | OCH₂-(1,3-dioxolan-2-yl) | CH₃ | H |
| 101 | F | Cl | O-(tetrahydropyran-4-yl) | CH₃ | H |
| 102 | F | Cl | O-(tetrahydrothiophen-3-yl) | CH₃ | H |
| 103 | F | Cl | O-(tetrahydrothiopyran-4-yl) | CH₃ | H |
| 104 | F | Cl | O-(tetrahydrothiopyran-4-yl SO₂) | CH₃ | H |
| 105 | F | Cl | O-(N-methylpyrrolidin-3-yl) | CH₃ | H |
| 106 | F | Cl | O-(tetrahydrothiophen-3-yl SO₂) | CH₃ | H |
| 107 | F | Cl | OSO₂N(CH₃)₂ | CH₃ | H |
| 108 | F | Cl | OSO₂C₆H₅ | CH₃ | H |
| 109 | F | Cl | OCH₂C≡CH | CH₂(CH₂)₂F | H |
| 110 | F | Cl | OCH₂C≡CH | CH₂SO₂CH₃ | H |
| 111 | F | Cl | OCH₂C≡CH | CH₂CH₂OCH₃ | H |
| 112 | F | Cl | OCH₂C≡CH | CH₃ | C₂H₅ |
| 113 | F | Cl | OH | H | H |
| 114[1] | F | Cl | OCH(CH₃)₂ | CH₃ | H |
| 115[2] | F | Cl | OCH₂C≡CH | CH₃ | H |
| 116[2] | F | Cl | OCH(CH₃)₂ | CH₃ | H |

TABLE 1-continued

Representative Compounds

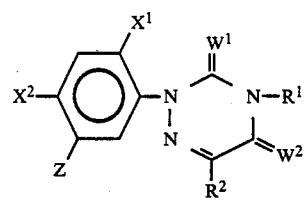

(Except where indicated otherwise, $W^1 = W^2$ = oxygen).

| Compound Number | $X^1$ | $X^2$ | Z | $R^1$ | $R^2$ |
|---|---|---|---|---|---|
| 117[3] | F | Cl | $OCH_2C\equiv CH$ | $CH_3$ | H |
| 118[3] | F | Cl | $OCH(CH_3)_2$ | $CH_3$ | H |
| 119 | F | Cl | $OCH(CH_3)_2$ | $CH_2OCH_3$ | H |
| 120 | F | Cl | $OCH(CH_3)_2$ | $CH_3$ | H |
| 121 | F | $OCH_3$ | $OCH(CH_3)_2$ | $CH_3$ | H |
| 122 | F | Cl | $O-CH_2$-cyclohexyl | $CH_3$ | H |
| 123 | F | Cl | $O$-cyclopropyl | $CH_3$ | H |
| 124 | F | Cl | $OCH_2SCH_3$ | $CH_3$ | H |
| 125 | F | Cl | $OCH_2CH=CH_2$ | $CH_3$ | H |
| 126 | F | Cl | $OCH_2C(Cl)=CH_2$ | $CH_3$ | H |
| 127 | F | Cl | $O-CO-CH_3$ | $CH_3$ | H |
| 128 | F | Cl | $OCH_2CO_2H$ | $CH_3$ | H |
| 129 | F | Cl | $OCH_2CO_2CH_3$ | $CH_3$ | H |
| 130 | F | Cl | $OCH_2CO_2CH_2$-cyclopropyl | $CH_3$ | H |
| 131 | F | Cl | $OCH_2CO_2CH_2$-cyclopentyl | $CH_3$ | H |
| 132 | F | Cl | $OCH_2CO_2CH_2$-cyclohexyl | $CH_3$ | H |
| 133 | F | Cl | $OCH_2CO_2$-cyclopropyl | $CH_3$ | H |
| 134 | F | Cl | $OCH_2CO_2$-cyclopentyl | $CH_3$ | H |
| 135 | F | Cl | $OCH_2CO_2$-cyclohexyl | $CH_3$ | H |
| 136 | F | Cl | $OCH_2CO_2$-(2-methylcyclohexyl) | $CH_3$ | H |
| 137 | F | Cl | $OCH_2CO_2-CH(CH_2)_5CH_2$ | $CH_3$ | H |

TABLE 1-continued

Representative Compounds

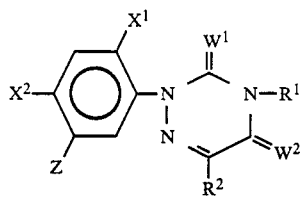

(Except where indicated otherwise, $W^1 = W^2 = $ oxygen).

| Compound Number | $X^1$ | $X^2$ | Z | $R^1$ | $R^2$ |
|---|---|---|---|---|---|
| 138 | F | Cl | $OCH_2CO-NH-CH_2OCH_3$ | $CH_3$ | H |
| 139 | F | Cl | $OCH_2CO-NH-CH_2SCH_3$ | $CH_3$ | H |
| 140 | F | Cl | $OCH_2CO_2CH_2CF_3$ | $CH_3$ | H |
| 141 | F | Cl | $OCH(CH_3)CO_2CH_2-CHCl_2$ | $CH_3$ | H |
| 142 | F | Cl | $OC(CH_3)_2CO_2CH_2-CH=CH_2$ | $CH_3$ | H |
| 143 | F | Cl | $OCH_2CO_2$-cyclohexenyl | $CH_3$ | H |
| 144 | F | Cl | $OCH_2CO_2CH_2$-cyclohexenyl | $CH_3$ | H |
| 145 | F | Cl | $OCH_2CO_2C_6H_5$ | $CH_3$ | H |
| 146 | F | Cl | $OCH_2CO_2CH_2C_6H_5$ | $CH_3$ | H |
| 147 | F | Cl | $OCH(CH_3)CO_2CH_2CN$ | $CH_3$ | H |
| 148 | F | Cl | $OCH_2CO_2CH_2C\equiv CH$ | $CH_3$ | H |
| 149 | F | Cl | $OCH_2CO_2N=C(CH_3)_2$ | $CH_3$ | H |
| 150 | F | Cl | $OCH_2CO_2N=CH$-cyclohexyl | $CH_3$ | H |
| 151 | F | Cl | $OCH_2CO_2N=$cyclopentylidene | $CH_3$ | H |
| 152 | F | Cl | $OCH_2CO_2N=$(2-methylcyclohexylidene) | H | H |
| 153[1] | F | Cl | $OCH(CH_3)_2$ | H | H |
| 154[2] | F | Cl | $OCH(CH_3)_2$ | H | H |
| 155[3] | F | Cl | $OCH(CH_3)_2$ | H | H |
| 156[1] | F | Cl | $OCH_2C\equiv CH$ | H | H |
| 157[2] | F | Cl | $OCH_2C\equiv CH$ | H | H |
| 158[3] | F | Cl | $OCH_2C\equiv CH$ | H | H |
| 159[1] | F | Cl | OH | H | H |
| 160[2] | F | Cl | OH | H | H |
| 161[3] | F | Cl | OH | H | H |
| 162[1] | F | Cl | OH | $CH_3$ | H |
| 163[2] | F | Cl | OH | $CH_3$ | H |
| 164[3] | F | Cl | OH | $CH_3$ | H |
| 165[1] | F | Cl | $OCH(CH_3)_2$ | H | $CO_2H$ |
| 166[2] | F | Cl | $OCH(CH_3)_2$ | H | $CO_2H$ |
| 167[3] | F | Cl | $OCH(CH_3)_2$ | H | $CO_2H$ |
| 168[1] | F | Cl | $OCH_2C\equiv CH$ | H | $CO_2H$ |
| 169[2] | F | Cl | $OCH_2C\equiv CH$ | H | $CO_2H$ |
| 170[3] | F | Cl | $OCH_2C\equiv CH$ | H | $CO_2H$ |
| 171[1] | F | Cl | $OCH(CH_3)_2$ | $CH_3$ | $CO_2H$ |
| 172[2] | F | Cl | $OCH(CH_3)_2$ | $CH_3$ | $CO_2H$ |
| 173[3] | F | Cl | $OCH(CH_3)_2$ | $CH_3$ | $CO_2H$ |
| 174[1] | F | Cl | $OCH_2C\equiv CH$ | $CH_3$ | $CO_2H$ |

TABLE 1-continued

Representative Compounds

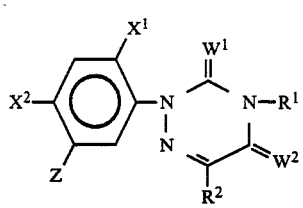

(Except where indicated otherwise, $W^1 = W^2 =$ oxygen).

| Compound Number | $X^1$ | $X^2$ | Z | $R^1$ | $R^2$ |
|---|---|---|---|---|---|
| 175[2] | F | Cl | OCH$_2$C≡CH | CH$_3$ | CO$_2$H |
| 176[3] | F | Cl | OCH$_2$C≡CH | CH$_3$ | CO$_2$H |
| 177 | F | Cl | OCH$_2$C≡CH | H | H |
| 178 | F | Cl | OCH(CH$_3$)$_2$ | H | CO$_2$H |
| 179 | F | Cl | OCH$_2$C≡CH | H | CO$_2$H |
| 180 | F | Cl | OCH(CH$_3$)$_2$ | CH$_3$ | CO$_2$H |
| 181 | F | Cl | OCH$_2$C≡CH | CH$_3$ | CO$_2$H |
| 182[1] | F | Cl | OCH(CH$_3$)$_2$ | CH$_3$ | H |
| 183 | F | Cl | OCH(CH$_3$)$_2$ | CH$_2$CH$_2$CH$_3$ | H |
| 184 | F | Cl | OCH(CH$_3$)$_2$ | CH$_2$CH$_2$F | H |
| 185 | F | Cl | OCH(CH$_3$)$_2$ | CH$_2$(CH$_2$)$_2$CH$_3$ | H |
| 186 | Cl | Cl | NH$_2$ | CH$_3$ | H |
| 187 | Cl | Cl | N(COCH$_3$)$_2$ | CH$_3$ | H |
| 188 | Cl | Cl | Cl | CH$_3$ | H |
| 189 | F | Cl | I | CH$_3$ | H |
| 190 | F | Cl | Cl | CH$_3$ | H |
| 191 | F | Cl | OCSN(CH$_2$CH$_3$)$_2$ | CH$_3$ | H |
| 192 | F | Cl | SCON(CH$_2$CH$_3$)$_2$ | CH$_3$ | H |
| 193 | F | Cl | OCH(CH$_3$)CO$_2$C(CH$_3$)$_3$ | CH$_3$ | H |
| 194 | F | Cl | NHN≡C(CH$_3$)$_2$ | CH$_3$ | H |
| 195 | F | Cl | OCH$_2$OCH$_2$CH$_2$OCH$_3$ | CH$_3$ | H |
| 196 | F | Cl | OCH(CH$_3$)$_2$ | CH$_2$SCH$_3$ | H |
| 197 | F | Cl | OCH(CH$_3$)$_2$ | CH$_2$SOCH$_3$ | H |
| 198 | F | Cl | OCH(CH$_3$)CO$_2$H | CH$_3$ | H |
| 199[1] | F | Br | OCH(CH$_3$)$_2$ | CH$_3$ | H |
| 200 | F | Cl | O(CH$_2$)$_2$CH$_3$ | CH$_3$ | H |
| 201 | F | Cl | O(CH$_2$)$_2$CH=CH$_2$ | CH$_3$ | H |
| 202 | F | Cl | OCH$_2$CN | CH$_3$ | H |
| 203[1] | F | Br | OCH$_2$C≡CH | CH$_3$ | H |
| 204[2] | F | Br | OCH$_2$C≡CH | CH$_3$ | H |
| 205[3] | F | Br | OCH$_2$C≡CH | CH$_3$ | H |
| 206 | F | Cl | NHCH(CH$_2$)$_4$CH (cyclic) | CH$_3$ | H |
| 207 | F | Cl | OCH(CH$_3$)CO$_2$CH(CH$_3$)$_2$ | CH$_3$ | H |
| 208 | F | Cl | OCH(CH$_3$)CO—SC$_2$H$_5$ | CH$_3$ | H |
| 209 | F | Cl | OCH(CH$_3$)C(O)NHSO$_2$-(4-Cl-C$_6$H$_4$) | CH$_3$ | H |
| 210 | F | Cl | OCH(CH$_3$)C(O)NHSO$_2$-(2-Cl-C$_6$H$_4$) | CH$_3$ | H |
| 211 | F | Cl | OCH$_3$ | CH$_3$ | H |
| 212 | F | Cl | OCH$_2$SOCH$_3$ | CH$_3$ | H |
| 213 | F | Cl | OCH$_2$SO$_2$CH$_3$ | CH$_3$ | H |
| 214 | F | Cl | F | H | H |
| 215 | F | Cl | F | CH$_3$ | H |
| 216[2] | F | Br | OCH(CH$_3$)$_2$ | CH$_3$ | H |
| 217[3] | F | Br | OCH(CH$_3$)$_2$ | CH$_3$ | H |
| 218 | F | Cl | SO$_2$Cl | CH$_3$ | H |

TABLE 1-continued

Representative Compounds

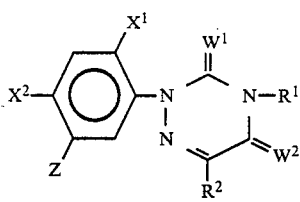

(Except where indicated otherwise, $W^1 = W^2$ = oxygen).

| Compound Number | $X^1$ | $X^2$ | Z | $R^1$ | $R^2$ |
|---|---|---|---|---|---|
| 219 | F | Cl | OCH(CH₃)C(O)S-C₆H₄-Cl | CH₃ | H |
| 220 | F | Cl | OCH(OC₂H₅)CO₂C₂H₅ | CH₃ | H |
| 221 | F | Cl | OCH(OCH₃)CO₂CH₃ | CH₃ | H |
| 222 | F | Cl | SCH(CH₃)C(O)NHSO₂-C₆H₄-Cl | CH₃ | H |
| 223 | F | Cl | SCH(CH₃)CO₂CH(CH₃)₂ | CH₃ | H |
| 224 | F | Cl | SCH(CH₂)₃CH (cyclic) | CH₃ | H |
| 225 | F | Cl | SCH₂OCH₃ | CH₃ | H |
| 226 | F | Cl | SCH₂CN | CH₃ | H |
| 227 | F | Br | OCH₂C≡CH | CH₃ | H |
| 228 | F | Cl | OCH(CH₃)C(O)NHSO₂-C₆H₄-OCH₃ | CH₃ | H |
| 229 | F | Cl | OCH₂Si(CH₃)₃ | CH₃ | H |
| 230 | F | Cl | OC₂H₅ | CH₃ | H |
| 231 | F | Cl | OCH(CH₃)C(O)NHSO₂-C₆H₄-CO₂CH₃ | CH₃ | H |
| 232 | F | Cl | NHCH(CH₃)CO₂C₂H₅ | CH₃ | H |
| 233 | F | Br | OCH(CH₃)CO₂CH(CH₃)₂ | CH₃ | H |
| 234 | F | Br | OCH₂OCH₃ | CH₃ | H |
| 235 | F | Br | OCH(CH₃)C(O)NHSO₂-C₆H₄-Cl | CH₃ | H |
| 236 | F | Cl | O(CH₂)₂F | CH₃ | H |
| 237 | F | Cl | OCH₂CF₃ | CH₃ | H |
| 238 | F | Cl | SCH₂-(tetrahydrofuran-2-yl) | CH₃ | H |
| 239 | F | Cl | OCH₂C≡CH | CHF₂ | H |
| 240 | F | Br | H | CH₃ | H |
| 241[1] | F | Br | H | CH₃ | H |
| 242[2] | F | Cl | H | CH₃ | H |
| 243 | F | Cl | OC(CH₃)₂CO₂C₂H₅ | CH₃ | H |

TABLE 1-continued

Representative Compounds

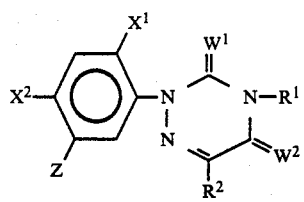

(Except where indicated otherwise, $W^1 = W^2 =$ oxygen).

| Compound Number | $X^1$ | $X^2$ | Z | $R^1$ | $R^2$ |
|---|---|---|---|---|---|
| 244 | F | Cl | OCH$_2$—⟨O,S⟩ (cyclic acetal with O and S) | CH$_3$ | H |
| 245 | F | Cl | CN | CH$_3$ | H |
| 246 | F | Cl | CH$_3$ | CH$_3$ | H |
| 247 | F | Cl | CF$_3$ | CH$_3$ | H |
| 248 | F | Cl | CO$_2$Na | CH$_3$ | H |
| 249 | F | Cl | SO$_3$Na | CH$_3$ | H |
| 250 | F | Br | OCH(CH$_3$)CO$_2$Na | CH$_3$ | H |
| 251 | F | Cl | OCH$_2$C≡CH | CH$_2$CONH$_2$ | H |
| 252 | F | Cl | OCH(CH$_3$)CONH$_2$ | CH$_3$ | H |
| 253 | F | Cl | OCH(CH$_3$)CONHSO$_2$—C$_6$H$_3$(C$_2$H$_5$)(OC$_2$H$_5$) | CH$_3$ | H |
| 254 | F | Cl | S—cyclopentyl | CH$_3$ | H |
| 255 | F | Cl | OCH(CH$_3$)CONSO$_2$—C$_6$H$_4$—Cl, Na$^⊕$ | CH$_3$ | H |
| 256 | F | Cl | OCH(CH$_3$)CONSO$_2$—C$_6$H$_4$—Cl, H$_3$NCH(CH$_3$)$_2^⊕$ | CH$_3$ | H |
| 257 | F | Cl | N(SO$_2$CH$_3$)$_2$ | CH$_3$ | H |
| 258 | F | Cl | NH(SO$_2$CH$_3$) | CH$_3$ | H |
| 259 | F | Cl | NHCH(CH$_2$)$_5$CH$_3$ with CH$_2$OH | CH$_3$ | H |
| 260 | F | Cl | NHCHCO$_2$C$_2$H$_5$ with CH(CH$_3$)$_2$ | CH$_3$ | H |
| 261 | F | Cl | OCH(CH$_3$)CONHSO$_2$—C$_6$H$_3$(OCH$_3$)(OCH$_3$) | CH$_3$ | H |

TABLE 1-continued

Representative Compounds

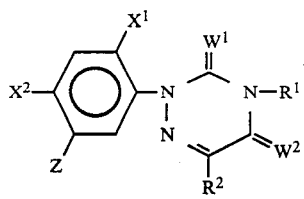

(Except where indicated otherwise, $W^1 = W^2 =$ oxygen).

| Compound Number | $X^1$ | $X^2$ | Z | $R^1$ | $R^2$ |
|---|---|---|---|---|---|
| 262 | F | Cl | OCH(CH₃)CONHSO₂—[phenyl with Br (para) and OCH₃] | CH₃ | H |
| 263 | F | Cl | OCH(CH₃)CONHSO₂—[phenyl with NO₂] | CH₃ | H |
| 264 | F | Cl | OCH(CH₃)CONHSO₂—[phenyl with two OCH₃] | CH₃ | H |
| 265 | F | Cl | OCH(CH₃)CON⁻SO₂ Na⁺—[phenyl with Br and OCH₃] | CH₃ | H |
| 266 | F | Cl | N(SO₂C₂H₅)₂ | CH₃ | H |
| 267 | F | Cl | NHSO₂C₂H₅ | CH₃ | H |
| 268 | F | Cl | OCH(CH₃)CONHSO₂—[phenyl with NO₂] | CH₃ | H |
| 269 | F | Cl | OCH(CH₃)CONHSO₂—[phenyl with CH₃ and OCH₃] | CH₃ | H |
| 270 | F | Cl | OCH(CH₃)CONHSO₂—[phenyl with F and CH₃O] | CH₃ | H |
| 271 | F | Cl | OCH(CH₃)CONHSO₂—[phenyl with F and OCH₃] | CH₃ | H |

TABLE 1-continued

Representative Compounds

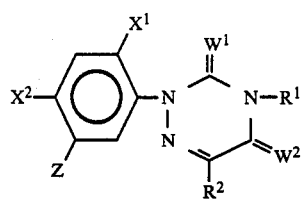

(Except where indicated otherwise, $W^1 = W^2 =$ oxygen).

| Compound Number | $X^1$ | $X^2$ | Z | $R^1$ | $R^2$ |
|---|---|---|---|---|---|
| 272 | F | Cl | O(CH$_2$)$_3$NHSO$_2$—C$_6$H$_4$—CH$_3$ | CH$_3$ | H |
| 273 | F | Cl | OCH(CH$_3$)CONHSO$_2$—C$_6$H$_4$—O—C(CH$_3$)$_2$CH$_3$ | CH$_3$ | H |
| 274 | F | Cl | OCH(CH$_3$)CONHSO$_2$—C$_6$H$_4$(O—)$_2$cyclohexane | CH$_3$ | H |
| 275 | F | Cl | OCH(CH$_3$)CONHSO$_2$—C$_6$H$_4$—CH$_3$ | CH$_3$ | H |
| 276 | F | Cl | N(SO$_2$C$_3$H$_7$)$_2$ | CH$_3$ | H |
| 277 | F | Cl | N(SO$_2$C$_4$H$_9$)$_2$ | CH$_3$ | H |
| 278 | F | Cl | NHSO$_2$C$_4$H$_9$ | CH$_3$ | H |
| 279 | F | Cl | NHSO$_2$C$_3$H$_7$ | CH$_3$ | H |
| 280 | F | Cl | OCH(CH$_3$)CONHSO$_2$—C$_6$H$_4$—OC$_4$H$_9$ | CH$_3$ | H |
| 281 | F | Cl | O(CH$_2$)$_3$NHSO$_2$CH$_3$ | CH$_3$ | H |
| 282 | F | Cl | O(CH$_2$)$_2$NHSO$_2$—C$_6$H$_4$—CH$_3$ | CH$_3$ | H |
| 283 | F | Cl | O(CH$_2$)$_2$NHSO$_2$CH$_3$ | CH$_3$ | H |
| 284 | F | Cl | OCH$_2$—C$_6$H$_4$—NO$_2$ | CH$_3$ | H |
| 285 | F | Cl | O(CH$_2$)$_3$O—C$_6$H$_5$ | CH$_3$ | H |

TABLE 1-continued

Representative Compounds

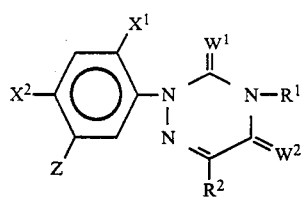

(Except where indicated otherwise, $W^1 = W^2 =$ oxygen).

| Compound Number | $X^1$ | $X^2$ | Z | $R^1$ | $R^2$ |
|---|---|---|---|---|---|
| 286 | F | Cl | OCH₂—N(phthalimide) | CH₃ | H |
| 287 | F | Cl | O(CH₂)₂N(CH₃)₂ | CH₃ | H |
| 288 | F | Cl | OCH(CH₃)C(O)NHSO₂-(2-CH₃-5-OC₂H₅-phenyl) | CH₃ | H |
| 289 | F | Cl | OCH(CH₃)C(O)NHSO₂-(2-C₂H₅-5-OCH₃-phenyl) | CH₃ | H |
| 290 | F | Br | OCH(CH₃)C(O)NHSO₂-(2-CH₃-5-OCH₃-phenyl) | CH₃ | H |
| 291 | F | Cl | NHCH(CH₃)CO₂CH₃ | CH₃ | H |
| 292 | F | Cl | ⊕NH₃Cl⊖ | CH₃ | H |
| 293 | F | Cl | O(CH₂)₃NHSO₂-(2-CH₃-5-OCH₃-phenyl) | CH₃ | H |
| 294 | F | Cl | OCH(CH₃)₂ | CH₃ | CH₃ |
| 295 | F | CF₃ | OCH(CH₃)C(O)NHSO₂-(2-CH₃-5-OCH₃-phenyl) | CH₃ | H |
| 296 | F | Br | NHSO₂C₂H₅ | CH₃ | H |
| 297 | Br | Br | NHSO₂C₂H₅ | CH₃ | H |
| 298 | F | Br | OH | CH₃ | H |
| 299 | F | Br | OC₂H₅ | CH₃ | H |
| 300 | F | Cl | —NHSO₂-phenyl | CH₃ | H |

TABLE 1-continued

Representative Compounds

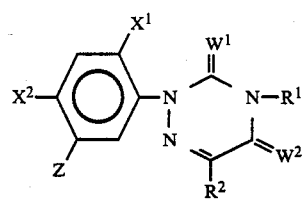

(Except where indicated otherwise, $W^1 = W^2 =$ oxygen).

| Compound Number | $X^1$ | $X^2$ | Z | $R^1$ | $R^2$ |
|---|---|---|---|---|---|
| 301 | F | Cl | —NHSO$_2$—⟨C$_6$H$_4$⟩—CH$_3$ | CH$_3$ | H |
| 302 | F | Cl | —NHSO$_2$—⟨C$_6$H$_4$⟩—Cl | CH$_3$ | H |
| 303 | F | Cl | —N(CH$_3$)SO$_2$CH$_3$ | CH$_3$ | H |
| 304 | F | Cl | —N(C$_2$H$_5$)SO$_2$CH$_3$ | CH$_3$ | H |
| 305 | F | Cl | —N(CH(CH$_3$)$_2$)SO$_2$CH$_3$ | CH$_3$ | H |
| 306 | F | Cl | —N(CH$_2$CH$_2$CH$_3$)SO$_2$CH$_3$ | CH$_3$ | H |
| 307 | F | Cl | —N(CH$_2$CH$_2$CH$_2$CH$_3$)SO$_2$CH$_3$ | CH$_3$ | H |
| 308 | F | Cl | —N(CH$_2$CH$_2$F)SO$_2$CH$_3$ | CH$_3$ | H |
| 309 | F | Cl | —N(CH$_2$CH$_2$CH$_2$F)SO$_2$CH$_3$ | CH$_3$ | H |
| 310 | F | Cl | —N(CH$_2$CH=CH$_2$)SO$_2$CH$_3$ | CH$_3$ | H |
| 311 | F | Cl | —N(CH$_2$C≡CH)SO$_2$CH$_3$ | CH$_3$ | H |
| 312 | F | Cl | —N(CH$_2$OCH$_3$)SO$_2$CH$_3$ | CH$_3$ | H |
| 313 | F | Cl | —N(CH$_2$C$_6$H$_5$)SO$_2$CH$_3$ | CH$_3$ | H |
| 314 | F | Cl | —N(CH$_3$)SO$_2$C$_2$H$_5$ | CH$_3$ | H |
| 315 | F | Cl | —N(CH$_2$H$_5$)SO$_2$C$_2$H$_5$ | CH$_3$ | H |
| 316 | F | Cl | —N(SO$_2$CH$_2$)(CH$_2$—CH$_2$) (cyclic) | CH$_3$ | H |
| 317 | F | Cl | —NHSO$_2$N(CH$_3$)$_2$ | CH$_3$ | H |
| 318 | F | Cl | —NKSO$_2$CH$_3$ | CH$_3$ | H |
| 319 | F | Cl | —NKSO$_2$C$_2$H$_5$ | CH$_3$ | H |
| 320 | F | Cl | —NHCH(CH$_3$)CH$_2$CO$_2$C$_2$H$_5$ | CH$_3$ | H |
| 321 | F | Cl | —NHCH$_2$—⟨C$_6$H$_4$⟩—CO$_2$CH$_3$ | CH$_3$ | H |
| 322 | F | Cl | —NH—CH(CH$_3$)C(O)OH | CH$_3$ | H |
| 323 | F | Cl | —NHCH$_2$CO$_2$C$_2$H$_5$ | CH$_3$ | H |
| 324 | F | Cl | —NH—CH$_2$C(O)—NHSO$_2$—⟨C$_6$H$_3$(OCH$_3$)(CH$_3$)⟩ | CH$_3$ | H |
| 325 | F | Cl | —NHCH$_2$C(O)—NHSO$_2$—⟨C$_6$H$_4$⟩—Cl | CH$_3$ | H |

TABLE 1-continued
Representative Compounds

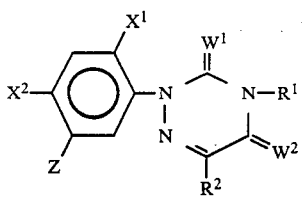

(Except where indicated otherwise, $W^1 = W^2$ = oxygen).

| Compound Number | $X^1$ | $X^2$ | Z | $R^1$ | $R^2$ |
|---|---|---|---|---|---|
| 326 | F | Cl | —NHCHCONHSO$_2$—⌬—Cl<br>  \|<br>  CH$_3$ | CH$_3$ | H |
|  |  |  |  | CH$_3$ | H |
| 327 | F | Cl | —NHOSO$_2$CH$_3$ | CH$_3$ | H |
| 328 | F | Cl | —NHOCH$_2$C≡CH | CH$_3$ | H |
| 329 | F | OCF$_2$H | —O—CH$_2$C≡CH | CH$_3$ | H |
| 330 | F | Cl | —NHCH$_2$—CH——CHCO$_2$C$_2$H$_5$<br>         \\  /<br>          CH$_2$ | CH$_3$ | H |
| 331 | F | Cl | $\quad\quad\quad\quad$ O<br>$\quad\quad\quad\quad$ ‖<br>—NHCH$_2$CH$_2$—SC$_2$H$_5$<br>$\quad\quad\quad\quad$ ‖<br>$\quad\quad\quad\quad$ O | CH$_3$ | H |
| 332 | F | Cl | —NHSO$_2$—⌬—O—C(CH$_3$)$_2$— | CH$_3$ | H |

$^1W^1 = O, W^2 = S$
$^2W^1 = S, W^2 = O$
$^3W^1 = W^2 = S$
$^4X^1 = 3$-Cl

Other representative compounds are identical with compound nos. 1–198, 200–202, 206–215, 218–226, 228–232, 236–239, 242–249, 251–289, 291–295, 300–332, respectively except that in each case $X^1$ is F and $X^2$ is Br. Other representative compounds are identical with compounds 1–3, 6, 7, 17–19, 21, 24, 30–50, 52–185, 189–332, respectively except that in each case, $X^1$ and $X^2$ are both Cl. Other representative compounds are identical with compounds 1–332, respectively, except that in each case $X^1$ is Cl and $X^2$ is Br. Other representative compounds are identical with compounds 1–332, respectively except that in each case $X^1$ is Br. Still other representative compounds are identical with compounds 1–328, 329, 332, respectively except that in each case $X^1$ is F and $X^2$ is OCF$_2$H. Still other representative compounds are identical with compounds 1–332, respectively, except that in each case $X^1$ is F and $X^2$ is OCF$_2$CF$_2$H. The compounds in which $X^2$ is OCF$_2$H or OCF$_2$CF$_2$H may be prepared, for example, by reacting compounds of this invention (or intermediates) in which $X^2$ is methoxy with ClCF$_2$H or ClCF$_2$CF$_2$H according to well known methods for replacing the methoxy group by a fluoroalkoxy group.

TABLE A-1
Representative Compounds

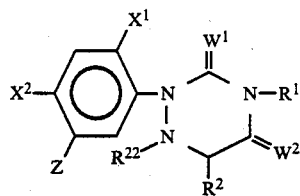

(Except where indicated otherwise, $W^1 = W^2 =$ oxygen).

| Compound Number | $X^1$ | $X^2$ | Z | $R^1$ | $R^2$ | $R^{22}$ |
|---|---|---|---|---|---|---|
| A-1 | Cl | H | H | $CH_3$ | H | H |
| A-2 | F | Cl | —SH | $CH_3$ | H | H |
| A-3 | F | Cl | —$OCH_2C$ CH | $CH_3$ | H | H |
| A-4 | F | Cl | —$NHCH(CH_3)CO_2C_2H_5$ | $CH_3$ | H | H |
| A-5 | F | Cl | —$OCH_2C\equiv CH$ | $CH_3$ | H | —$COCH_3$ |
| A-6 | F | Cl | —$OC_2H_5$ | $CH_3$ | H | H |
| A-7 | F | Cl | —$NHSO_2CH_3$ | $CH_3$ | H | H |
| A-8 | F | Cl | 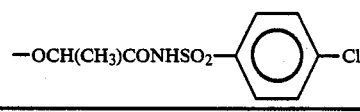 | $CH_3$ | H | H |

Other representative compounds are identical with each of the compounds listed in Table 1 and in the modifications as to $X^1$ and $X^2$ described below that Table 1, except that in each case the triazine ring is saturated (as in the compounds of Table A-1 above) and $R^2$ and $R^{22}$ are both hydrogen.

TABLE 2
Characterizing Data

| Compound Number | M.P.(°C.) | Empirical Formula | | Elemental Analysis | | |
|---|---|---|---|---|---|---|
| | | | | C | H | N |
| 60 | solid | $C_{13}H_{14}ClFN_4O_2$ | C | 49.93 | 4.51 | 17.92 |
| | | | F | 50.55 | 4.55 | 17.31 |
| 83 | 164–166 | $C_{12}H_{11}ClFN_3O_4S$ | C | 41.45 | 3.19 | 12.08 |
| | | | F | 41.45 | 3.07 | 11.67 |
| 84 | 154–156 | $C_{12}H_{11}ClFN_3O_5S$ | C | 39.62 | 3.05 | 11.55 |
| | | | F | 39.30 | 3.15 | 11.13 |
| 97 | 121–123 | $C_{14}H_{13}ClFN_3O_4$ | C | 49.21 | 3.83 | 12.29 |
| | | | F | 49.30 | 3.55 | 12.25 |
| 128 | 123–125 | $C_{13}H_{11}ClFN_3O_5$ | C | 45.43 | 3.23 | 12.23 |
| | | | F | 45.14 | 3.23 | 11.95 |
| 251 | 183–184 | $C_{14}H_{10}ClFN_4O_4$ | C | 47.67 | 2.86 | 15.88 |
| | | | F | 47.87 | 2.98 | 15.85 |
| 252 | foam | $C_{13}H_{11}ClFN_4O_4$ | C | 45.56 | 3.53 | 16.35 |
| | | | F | 45.18 | 3.90 | 15.60 |
| 254 | 51–53 | $C_{15}H_{15}ClFN_3O_2S$ | | | | |
| 255 | solid | $C_{19}H_{14}Cl_2FN_4O_6S$ Na | | | | |
| 256 | foam | $C_{22}H_{24}Cl_2FN_5O_6S$ | | | | |
| 257 | 211–215 | $C_{12}H_{12}ClFN_4O_6S_2$ | C | 33.77 | 2.83 | 13.13 |
| | | | F | 33.00 | 3.06 | 12.26 |
| 258 | 70(dec) | $C_{11}H_{10}ClFN_4O_4S$ | C | 37.89 | 2.89 | 16.07 |
| | | | F | 38.30 | 2.85 | 15.16 |
| 259 | oil | $C_{18}H_{24}ClFN_4O_3$ | | | | |
| 260 | oil | $C_{17}H_{20}ClFN_4O_4$ | | | | |
| 261 | 194–195 | $C_{21}H_{20}ClFN_4O_8S$ | C | 46.46 | 3.71 | 10.31 |
| | | | F | 45.70 | 3.81 | 9.95 |
| 262 | foam | $C_{20}H_{17}BrClFN_4O_7S$ | | | | |
| 263 | foam | $C_{19}H_{15}ClFN_5O_8S$ | | | | |
| 264 | foam | $C_{21}H_{20}ClFN_4O_8S$ | | | | |
| 265 | foam | $C_{20}H_{16}BrClFN_4O_7S$ Na | | | | |
| 266 | foam | $C_{14}H_{16}ClFN_4O_6S$ | C | 36.97 | 3.55 | 12.32 |
| | | | F | 37.63 | 3.35 | 13.80 |
| 267 | 188–190 | $C_{12}H_{12}ClFN_4O_4S$ | C | 39.73 | 3.33 | 15.44 |
| | | | F | 39.90 | 3.61 | 15.54 |

TABLE 2-continued
Characterizing Data

| Compound Number | M.P.(°C.) | Empirical Formula | | Elemental Analysis | | |
|---|---|---|---|---|---|---|
| | | | | C | H | N |
| 268 | foam | $C_{19}H_{15}ClFN_5O_8S$ | | | | |
| 269 | foam | $C_{21}H_{20}ClFN_4O_6S$ | | | | |
| 270 | foam | $C_{20}H_{17}ClFN_4O_7S$ | | | | |
| 271 | solid | $C_{20}H_{17}ClFN_4O_7S$ | | | | |
| 272 | foam | | | | | |
| 273 | 80–83(dec) | $C_{23}H_{22}ClFN_4O_7S$ | | | | |
| 274 | 123–124 (dec) | $C_{25}H_{24}ClFN_4O_8S$ | | | | |
| 275 | 193–195 | $C_{20}H_{18}ClFN_4O_6S$ | | | | |
| 276 | foam | $C_{16}H_{20}ClFN_4O_6S_2$ | C | 39.79 | 4.17 | 11.60 |
| | | | F | 38.46 | 4.03 | 10.79 |
| 277 | foam | $C_{18}H_{24}ClFN_4O_6S_2$ | C | 42.31 | 4.73 | 10.96 |
| | | | F | 42.34 | 4.52 | 10.69 |
| 278 | 128–131 | $C_{14}H_{16}ClFN_4O_4S$ | C | 43.03 | 4.13 | 14.34 |
| | | | F | 42.85 | 4.04 | 14.05 |
| 279 | 171–174 | $C_{13}H_{14}ClFN_4O_4S$ | C | 41.44 | 3.75 | 14.87 |
| | | | F | 41.38 | 3.65 | 14.65 |
| 280 | 127.5–129.5 (dec) | $C_{23}H_{24}ClFN_4O_7S$ | C | 49.75 | 4.34 | 10.09 |
| | | | F | 48.27 | 4.46 | 9.33 |
| 281 | 145–147 | $C_{14}H_{16}ClFN_4O_5S$ | C | 41.33 | 3.96 | 13.77 |
| | | | F | 41.41 | 4.25 | 13.49 |
| 282 | foam | $C_{19}H_{18}ClFN_4O_5S$ | C | 48.67 | 3.87 | 11.95 |
| | | | F | 48.28 | 4.15 | 11.11 |
| 283 | 133–135 | $C_{13}H_{14}ClFN_4O_5S$ | C | 39.75 | 3.59 | 14.26 |
| | | | F | 39.64 | 3.80 | 13.95 |
| 284 | 176–177 | $C_{17}H_{12}ClFN_4O_5$ | | | | |
| 285 | 77–78 | $C_{19}H_{17}ClFN_3O_4$ | C | 56.24 | 4.22 | 10.35 |
| | | | F | 55.75 | 4.15 | 10.16 |
| 286 | solid | $C_{19}H_{12}ClFN_4O_5$ | | | | |
| 287 | oil | $C_{14}H_{16}ClFN_4O_3$ | | | | |
| 291 | oil | $C_{14}H_{14}ClFN_4O_4$ | | | | |
| 292 | solid | $C_{10}H_9Cl_2FN_3O_2$ | | | | |
| 293 | foam | $C_{21}H_{22}ClFN_4O_6S$ | | | | |
| 294 | oil | $C_{14}H_{15}ClFN_3O_3$ | | | | |
| 298 | 193(dec) | $C_{10}H_7BrFN_3O_3$ | | | | |
| 299 | 114–115 | $C_{12}H_{11}BrFN_3O_3$ | | | | |
| 294 | oil | $C_{14}H_{15}ClFN_3O_3$ | | | | |
| 320 | oil | $C_{16}H_{18}ClFN_4O_4$ | | | | |
| 321 | foam | $C_{19}H_{16}ClFN_4O_4$ | | | | |
| 330 | oil | $C_{17}H_{18}ClFN_4O_4$ | | | | |

TABLE A-2
Characterizing Data

| Compound Number | M.P.(°C.) | Empirical Formula | | Elemental Analysis | | |
|---|---|---|---|---|---|---|
| | | | | C | H | N |
| A-1 | 118–120 | $C_{10}H_9Cl_2N_3O_2$ | C | 43.82 | 3.31 | 15.33 |
| | | | F | 44.01 | 3.43 | 15.04 |
| A-2 | 121–123 | $C_{10}H_9ClFN_3O_2S$ | C | 41.86 | 3.13 | 14.50 |
| | | | F | 41.74 | 3.05 | 14.24 |
| A-3 | oil | $C_{13}H_{11}ClFN_3O_3$ | | | | |
| A-4 | — | $C_{15}H_{18}ClFN_4O_4$ | | | | |
| A-5 | 160–161 | $C_{15}H_{13}ClFN_3O_4$ | C | 50.93 | 3.70 | 11.88 |
| | | | F | 51.10 | 3.84 | 11.74 |

TABLE 3
Preemergence Herbicidal Activity

| Compound No. | 60 | 83 | 84 | 97 | 128 |
|---|---|---|---|---|---|
| Rate (kg/ha) | 0.5 | 2.0 | 4.0 | 0.5 | 1.0 |
| Species | % C | % C | % C | % C | % C |
| Cotton | 70 | 100 | 100 | 100 | 100 |
| Soybean | 80 | 100 | 100 | 90 | 95 |
| Field Corn | 95 | 100 | 100 | 100 | 50 |
| Rice | 80 | 100 | 100 | 90 | 70 |
| Wheat | 95 | 100 | 100 | 80 | 80 |
| Field Bindweed | 80 | 100 | 100 | 70 | 90 |
| Morningglory | 40 | 100 | 100 | 70 | 100 |
| Velvetleaf | 100 | 100 | 100 | 100 | 100 |
| Barnyardgrass | 95 | 100 | 100 | 90 | 100 |
| Green Foxtail | 100 | 100 | 100 | 100 | 100 |
| Johnsongrass | 100 | 100 | 100 | 90 | 95 |
| Nutsyell | — | 100 | 100 | 80 | 80 |

| Compound No. | 251 | 252 | 254 | 255 | 256 |
|---|---|---|---|---|---|
| Rate (kg/ha) | 4.0 | 2.0 | 1.0 | 1.0 | 1.0 |
| Species | % C | % C | % C | % C | % C |
| Cotton | 60 | 100 | 30 | 95 | 100 |
| Soybean | 50 | 100 | 70 | 40 | 90 |
| Field Corn | 90 | 100 | 80 | 20 | 70 |
| Rice | — | — | — | — | — |
| Wheat | 30 | 100 | 20 | 10 | 30 |
| Field Bindweed | 70 | 100 | 20 | 90 | 100 |
| Morningglory | 90 | 100 | 90 | 95 | 100 |
| Velvetleaf | 100 | 100 | 100 | 100 | 100 |
| Barnyardgrass | 30 | 100 | 100 | 60 | 100 |
| Green Foxtail | 80 | 100 | 100 | 90 | 100 |
| Johnsongrass | 60 | 100 | 80 | 60 | 95 |
| Nutsyell | 20 | 100 | 10 | — | — |

| Compound No. | 257 | 258 | 259 | 260 | 261 |
|---|---|---|---|---|---|
| Rate (kg/ha) | 1.0 | 1.0 | 2.0 | 0.25 | 0.5 |
| Species | % C | % C | % C | % C | % C |
| Cotton | 100 | 100 | 20 | 0 | 100 |
| Soybean | 95 | 95 | 80 | 20 | 95 |
| Field Corn | 95 | 95 | 20 | 10 | 30 |
| Rice | — | — | — | — | — |
| Wheat | 80 | 70 | 20 | 20 | 50 |
| Field Bindweed | 100 | 100 | 40 | 30 | 100 |
| Morningglory | 100 | 100 | 70 | 0 | 100 |
| Velvetleaf | 100 | 100 | 50 | 30 | 100 |
| Barnyardgrass | 100 | 100 | 20 | 100 | 95 |
| Green Foxtail | 100 | 100 | 50 | 60 | 90 |
| Johnsongrass | 100 | 95 | 20 | 40 | 95 |

| Compound No. | 262 | 263 | 264 | 265 | 266 |
|---|---|---|---|---|---|
| Rate (kg/ha) | 0.5 | 0.5 | 0.5 | 0.5 | 0.5 |
| Species | % C | % C | % C | % C | % C |
| Cotton | 70 | 40 | 95 | 30 | 95 |
| Soybean | 70 | 30 | 90 | 20 | 70 |
| Field Corn | 40 | 10 | 20 | 0 | 100 |
| Rice | — | — | — | — | — |
| Wheat | 50 | 40 | 30 | 0 | 50 |
| Field Bindweed | 100 | 95 | 100 | 100 | 100 |
| Morningglory | 100 | 50 | 95 | 50 | 95 |
| Velvetleaf | 100 | 100 | 100 | 100 | 100 |
| Barnyardgrass | 100 | 70 | 95 | 0 | 100 |
| Green Foxtail | 100 | 100 | 40 | 0 | 100 |
| Johnsongrass | 100 | 60 | 95 | 90 | 80 |

| Compound No. | 267 | 268 | 270 | 272 | 273 |
|---|---|---|---|---|---|
| Rate (kg/ha) | 1.0 | 2.0 | 2.0 | 2.0 | 0.125 |
| Species | % C | % C | % C | % C | % C |
| Cotton | 100 | 50 | 100 | 40 | 10 |
| Soybean | 95 | 50 | 100 | 40 | 10 |
| Field Corn | 80 | 10 | 100 | 90 | 10 |
| Rice | — | — | — | — | — |
| Wheat | 60 | 50 | 100 | 20 | 0 |
| Field Bindweed | 100 | 100 | 100 | 100 | 90 |
| Morningglory | 100 | 100 | 100 | 100 | 20 |
| Velvetleaf | 100 | 100 | 100 | 100 | 100 |
| Barnyardgrass | 100 | 100 | 100 | 100 | 10 |
| Green Foxtail | 100 | 100 | 100 | 100 | 30 |
| Johnsongrass | 70 | 70 | 100 | 95 | 20 |

| Compound No. | 274 | 275 | 276 | 277 | 278 |
|---|---|---|---|---|---|
| Rate (kg/ha) | 0.5 | 0.25 | 1.0 | 1.0 | 1.0 |
| Species | % C | % C | % C | % C | % C |
| Cotton | 30 | 90 | 60 | 20 | 90 |
| Soybean | 20 | 70 | 40 | 20 | 40 |
| Field Corn | 10 | 20 | 95 | 70 | 90 |
| Rice | — | — | — | — | — |
| Wheat | 0 | 20 | 95 | 20 | 20 |
| Field Bindweed | 70 | 100 | 100 | 100 | 100 |
| Morningglory | 0 | 100 | 100 | 80 | 100 |
| Velvetleaf | 95 | 100 | 100 | 100 | 100 |
| Barnyardgrass | 0 | 50 | 100 | 100 | 100 |
| Green Foxtail | 10 | 10 | 100 | 100 | 100 |
| Johnsongrass | 10 | 40 | 100 | 90 | 95 |

| Compound No. | 279 | 280 | 281 | 282 | 283 |
|---|---|---|---|---|---|
| Rate (kg/ha) | 1.0 | 0.25 | 0.25 | 0.25 | 2.0 |
| Species | % C | % C | % C | % C | % C |
| Cotton | 95 | 10 | 10 | 70 | 20 |
| Soybean | 90 | 0 | 10 | 30 | 10 |
| Field Corn | 90 | 10 | 10 | 60 | 10 |
| Rice | — | — | — | — | — |
| Wheat | 20 | 10 | 0 | 10 | 10 |
| Field Bindweed | 100 | 20 | 0 | 80 | 40 |
| Morningglory | 100 | 10 | 10 | 80 | 60 |
| Velvetleaf | 100 | 60 | 80 | 100 | 90 |
| Barnyardgrass | 100 | 20 | 10 | 80 | 20 |
| Green Foxtail | 100 | 30 | 40 | 90 | 40 |
| Johnsongrass | 90 | 30 | 0 | 40 | 30 |

| Compound No. | 284 | 285 | 286 | 287 | 292 |
|---|---|---|---|---|---|
| Rate (kg/ha) | 2.0 | 2.0 | 2.0 | 4.0 | 8.0 |
| Species | % C | % C | % C | % C | % C |
| Cotton | 0 | 70 | 10 | 20 | — |
| Soybean | 0 | 90 | 90 | 0 | 100 |
| Field Corn | 20 | 30 | 90 | 50 | 75 |
| Rice | — | — | — | — | — |
| Wheat | 20 | 50 | 50 | 0 | 75 |
| Field Bindweed | 0 | 100 | 80 | 20 | 30 |
| Morningglory | 30 | 95 | 70 | 95 | 100 |
| Velvetleaf | 30 | 100 | 100 | 30 | 40 |
| Barnyardgrass | 10 | 100 | 95 | 0 | 80 |
| Green Foxtail | 100 | 100 | 100 | 20 | — |
| Johnsongrass | 0 | 60 | 70 | 20 | — |

| Compound No. | | 294 | 298 | 299 | |
|---|---|---|---|---|---|
| Rate (kg/ha) | | 0.25 | 4.0 | 0.25 | |
| Species | | % C | % C | % C | |
| Cotton | | 80 | 80 | 30 | |
| Soybean | | 0 | 70 | 10 | |
| Field Corn | | 80 | 95 | 95 | |
| Rice | | — | — | — | |
| Wheat | | 30 | 90 | 100 | |
| Field Bindweed | | 30 | 80 | — | |
| Morningglory | | 50 | 95 | 100 | |
| Velvetleaf | | 50 | 100 | 100 | |
| Barnyardgrass | | 80 | 100 | 100 | |
| Green Foxtail | | 100 | 100 | 100 | |
| Johnsongrass | | 80 | 95 | 95 | |

| Compound No. | A-1 | A-2 | A-3 | A-4 | A-5 |
|---|---|---|---|---|---|
| Rate (kg/ha) | 8.0 | 8.0 | 4.0 | 4.0 | 4.0 |
| Species | % C | % C | % C | % C | % C |
| Cotton | 70 | 30 | 100 | 100 | 0 |
| Soybean | 80 | 0 | 60 | 90 | 30 |
| Field Corn | 100 | 70 | 100 | 30 | 60 |

TABLE 3-continued

| Preemergence Herbicidal Activity | | | | | |
|---|---|---|---|---|---|
| Rice | — | — | — | — | — |
| Wheat | 80 | 20 | 100 | 100 | 70 |
| Field Bindweed | 95 | 40 | — | 100 | 50 |
| Morningglory | 100 | 70 | 100 | 100 | 50 |
| Velvetleaf | 100 | 100 | 100 | 100 | 95 |
| Barnyardgrass | 95 | 80 | 100 | 100 | 95 |
| Green Foxtail | 100 | 100 | 100 | 100 | 100 |
| Johnsongrass | 100 | 100 | 100 | 100 | 90 |

TABLE 4

| Postemergence Herbicidal Acitivity | | | | | |
|---|---|---|---|---|---|
| Compound No. | 60 | 83 | 84 | 97 | 128 |
| Rate (kg/ha) | 0.5 | 2.0 | 4.0 | 0.5 | 1.0 |
| Species | % C | % C | % C | % C | % C |
| Cotton | 80 | 100 | 100 | 100 | 100 |
| Soybean | 90 | 100 | 100 | 70 | 100 |
| Field Corn | 95 | 100 | 100 | 80 | 95 |
| Rice | — | — | — | — | — |
| Wheat | 80 | 100 | 100 | 80 | 100 |
| Field Bindweed | 70 | 100 | 100 | 100 | 100 |
| Morningglory | 60 | 100 | 100 | 80 | 100 |
| Velvetleaf | 100 | 100 | 100 | 100 | 100 |
| Barnyardgrass | 90 | 100 | 100 | 100 | 100 |
| Green Foxtail | 90 | 100 | 100 | 100 | 100 |
| Johnsongrass | 90 | 100 | 100 | 90 | 100 |
| Nutsyell | — | 100 | 100 | 60 | 90 |
| Compound No. | 251 | 252 | 254 | 257 | 258 |
| Rate (kg/ha) | 4.0 | 2.0 | 1.0 | 1.0 | 1.0 |
| Species | % C | % C | % C | % C | % C |
| Cotton | 60 | 100 | 100 | 100 | 100 |
| Soybean | 30 | 100 | 80 | 90 | 100 |
| Field Corn | 10 | 90 | 40 | 80 | 80 |
| Rice | — | — | — | — | — |
| Wheat | 0 | 80 | 40 | 50 | 50 |
| Field Bindweed | 60 | 100 | 60 | 100 | 100 |
| Morningglory | 10 | 100 | 50 | 100 | 100 |
| Velvetleaf | 40 | 100 | 100 | 100 | 100 |
| Barnyardgrass | 0 | 100 | 10 | 100 | 100 |
| Green Foxtail | 80 | 100 | 40 | 100 | 100 |
| Johnsongrass | 70 | 100 | 10 | 95 | 90 |
| Nutsyell | 0 | 70 | 10 | — | — |
| Compound No. | 259 | 260 | 261 | 262 | 263 |
| Rate (kg/ha) | 2.0 | 0.25 | 0.5 | 0.5 | 0.5 |
| Species | % C | % C | % C | % C | % C |
| Cotton | 95 | 90 | 100 | 100 | 100 |
| Soybean | 95 | 80 | 100 | 100 | 80 |
| Field Corn | 60 | 60 | 70 | 100 | 20 |
| Rice | — | — | — | — | — |
| Wheat | 10 | 40 | 100 | 100 | 20 |
| Field Bindweed | 80 | 50 | 100 | 100 | 50 |
| Morningglory | 95 | 60 | 100 | 100 | 60 |
| Velvetleaf | 100 | 100 | 100 | 100 | 100 |
| Barnyardgrass | 20 | 40 | 100 | 80 | 80 |
| Green Foxtail | 20 | 30 | 100 | 95 | 80 |
| Johnsongrass | 50 | 30 | 100 | 100 | 70 |
| Compound No. | 264 | 265 | 266 | 267 | 269 |
| Rate (kg/ha) | 0.5 | 0.5 | 0.5 | 1.0 | 0.5 |
| Species | % C | % C | % C | % C | % C |
| Cotton | 100 | 90 | 100 | 100 | 40 |
| Soybean | 100 | 95 | 80 | 100 | 85 |
| Field Corn | 60 | 70 | 80 | 60 | 98 |
| Rice | — | — | — | — | — |
| Wheat | 100 | 90 | 40 | 50 | 100 |
| Field Bindweed | 100 | 100 | 95 | 100 | 70 |
| Morningglory | 100 | 100 | 100 | 100 | 100 |
| Velvetleaf | 100 | 100 | 100 | 100 | 100 |
| Barnyardgrass | 90 | 10 | 100 | 100 | 100 |
| Green Foxtail | 100 | 40 | 95 | 100 | 90 |
| Johnsongrass | 100 | 95 | 90 | 95 | 90 |
| Compound No. | 271 | 273 | 274 | 275 | 276 |
| Rate (kg/ha) | 0.5 | 0.125 | 0.5 | 0.25 | 1.0 |
| Species | % C | % C | % C | % C | % C |
| Cotton | 10 | 80 | 95 | 100 | 90 |
| Soybean | 50 | 70 | 80 | 95 | 90 |
| Field Corn | 60 | 70 | 100 | 50 | 100 |
| Rice | — | — | — | — | — |
| Wheat | 100 | 95 | 50 | 100 | 80 |
| Field Bindweed | 100 | 90 | 30 | 100 | 95 |
| Morningglory | 100 | 90 | 90 | 100 | 100 |
| Velvetleaf | 100 | 100 | 90 | 90 | 100 |
| Barnyardgrass | 100 | 80 | 60 | 80 | 100 |
| Green Foxtail | 80 | 40 | 70 | 80 | 100 |
| Johnsongrass | 80 | 80 | 60 | 80 | 95 |
| Compound No. | 277 | 278 | 279 | 280 | 281 |
| Rate (kg/ha) | 1.0 | 1.0 | 1.0 | 0.25 | 0.25 |
| Species | % C | % C | % C | % C | % C |
| Cotton | 70 | 95 | 100 | 90 | 40 |
| Soybean | 70 | 60 | 80 | 60 | 30 |
| Field Corn | 70 | 60 | 70 | 100 | 20 |
| Rice | — | — | — | — | — |
| Wheat | 20 | 30 | 30 | 20 | 20 |
| Field Bindweed | 95 | 100 | 100 | 60 | 90 |
| Morningglory | 100 | 100 | 100 | 90 | 70 |
| Velvetleaf | 100 | 100 | 100 | 100 | 90 |
| Barnyardgrass | 95 | 100 | 100 | 70 | 30 |
| Green Foxtail | 100 | 100 | 100 | 70 | 30 |
| Johnsongrass | 95 | 90 | 80 | 30 | 20 |
| Compound No. | 282 | 283 | 284 | 285 | 286 |
| Rate (kg/ha) | 0.25 | 0.25 | 2.0 | 2.0 | 2.0 |
| Species | % C | % C | % C | % C | % C |
| Cotton | 100 | 70 | 60 | 100 | 80 |
| Soybean | 90 | 60 | 60 | 100 | 95 |
| Field Corn | 60 | 30 | 30 | 100 | 90 |
| Rice | — | — | — | — | — |
| Wheat | 10 | 10 | 30 | 50 | 80 |
| Field Bindweed | 80 | 80 | 40 | 100 | 100 |
| Morningglory | 100 | 100 | 50 | 100 | 100 |
| Velvetleaf | 100 | 90 | 100 | 100 | 100 |
| Barnyardgrass | 30 | 20 | 40 | 100 | 80 |
| Green Foxtail | 80 | 70 | 40 | 100 | 100 |
| Johnsongrass | 30 | 10 | 50 | 100 | 90 |
| Compound No. | 287 | 292 | 294 | 298 | 299 |
| Rate (kg/ha) | 4.0 | 8.0 | 0.5 | 4.0 | 0.25 |
| Species | % C | % C | % C | % C | % C |
| Cotton | 70 | — | 80 | 80 | 100 |
| Soybean | 95 | 100 | 70 | 90 | 80 |
| Field Corn | 20 | 75 | 30 | 95 | 90 |
| Rice | — | — | — | — | — |
| Wheat | 20 | 75 | 30 | 90 | 40 |
| Field Bindweed | 60 | — | 30 | 80 | 60 |
| Morningglory | 60 | 95 | 50 | 80 | 100 |
| Velvetleaf | 70 | 100 | 70 | 100 | 100 |
| Barnyardgrass | 20 | 95 | 30 | 95 | 80 |
| Green Foxtail | 50 | 40 | 95 | 100 | 100 |
| Johnsongrass | 10 | — | 90 | 60 | 70 |
| Compound No. | A-1 | A-2 | A-3 | A-4 | A-5 |
| Rate (kg/ha) | 8.0 | 8.0 | 4.0 | 4.0 | 0.5 |
| Species | % C | % C | % C | % C | % C |
| Cotton | 70 | 100 | 100 | 100 | 60 |
| Soybean | 80 | 60 | 90 | 100 | 80 |
| Field Corn | 70 | 30 | 100 | 100 | 80 |
| Rice | — | — | 100 | 95 | 70 |
| Wheat | 70 | 50 | 100 | 100 | 80 |
| Field Bindweed | 95 | 100 | — | 100 | 90 |
| Morningglory | 100 | 90 | 100 | 100 | 90 |
| Velvetleaf | 100 | 100 | 100 | 100 | 70 |
| Barnyardgrass | 100 | 100 | 100 | 100 | 90 |
| Green Foxtail | 100 | 100 | 100 | 100 | 80 |
| Johnsongrass | 100 | 100 | 100 | 100 | 80 |

| Paddy Rice Test | | |
|---|---|---|
| Compound No. | 209 | 272 |
| Rate (kg/ha) | 0.25 | 0.25 |
| Species | %.C | % C |
| Rice-Mars | 30 | 30 |
| Rice-Labelle | 30 | 20 |
| Hemp Sesbania | 90 | 90 |
| Flatsedge Rice | 100 | 100 |
| Barnyardgrass | 100 | 100 |
| Green Sprangletop | 100 | 100 |

We claim:
1. An herbicidal compound of the formula

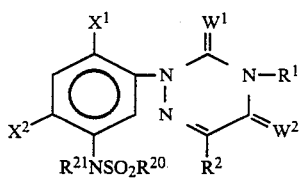

or

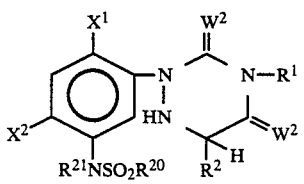

wherein W¹ and W² are independently oxygen or sulfur;
R¹ is alkyl of 1 to 6 carbon atoms, haloalkyl of 1 to 5 carbon atoms, cyanoalkyl of 1 to 5 alkyl carbon atoms, alkenyl or alkynyl of 2 to 5 carbon atoms, alkoxyalkyl, alkylthioalkyl, alkylsulfinylalkyl, or alkylsulfonylalkyl of 2 to 5 carbon atoms, or amino;
R² is hydrogen or alkyl of 1 to 4 carbon atoms;
X¹ is fluorine or chlorine;
X² is fluorine, chlorine, bromine, alkyl of 1 to 6 carbon atoms, haloalkyl of 1 to 5 carbon atoms, or alkoxy of 1 to 6 carbon atoms;
R²⁰ is lower alkyl, or phenyl which is substituted or unsubstituted with one or more groups selected from halogen, lower alkyl, lower alkoxy, cyano, cyanomethyl, nitro, amino, phenylamino, alkylamino of less than 6 carbon atoms, dialkylamino in which each alkyl is of less than 6 carbon atoms, hydroxycarbonyl, alkoxycarbonyl of less than 6 alkyl carbon atoms, alkoxyalkyl of 2 to 4 carbon atoms, alkoxycarbonylalkyl in which each alkyl is of less than 6 carbon atoms, benzyl, or hydroxy;
R²¹ is hydrogen, a salt-forming group, benzyl, alkyl, haloalkyl, alkoxy, alkynyl or alkenyl each having less than 6 alkyl carbon atoms, SO₂R²⁰, a group of the formula -alkylene-SO₂R²⁰ wherein the alkylene group has 1 to 4 carbon atoms, alkoxymethyl having less than 6 carbon atoms, cyanomethyl, ethoxycarbonylmethyl or R²⁰ and R²¹ together is alkylene of less than 6 carbon atoms.

2. A compound as in claim 1 in which X¹ and X² are each halogen, R¹ is CH₃, R²⁰ is lower alkyl and R²¹ is hydrogen, a salt-forming group, lower alkyl or —SO₂R²⁰.

3. A compound as in claim 2 in which X¹ is Cl or F, X² is Cl or Br, R²⁰ is lower alkyl and R²¹ is H or a salt-forming group.

4. A compound as in claim 2 in which R²⁰ is lower alkyl and R²¹ is —SO₂R²⁰.

5. A compound as in claim 2 in which R²⁰ is lower alkyl and R²¹ is lower alkyl.

6. An herbicidal composition comprising an herbicidally effective amount of the compound of claim 2 in admixture with a suitable carrier.

7. A method for controlling undesired plant growth which comprises applying to the locus where control is desired an herbicidally effective amount of the composition of claim 6.

8. An herbicidal compound of the formula

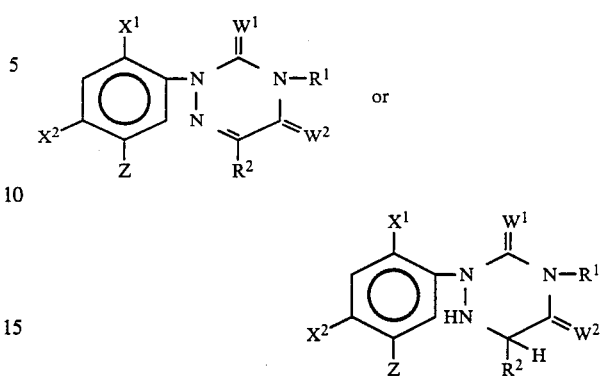

wherein W¹ and W² are independently oxygen or sulfur;
R¹ is alkyl of 1 to 6 carbon atoms, haloalkyl of 1 to 5 carbon atoms, cyanoalkyl of 1 to 5 alkyl carbon atoms, alkenyl or alkynyl of 2 to 5 carbon atoms, alkoxyalkyl, alkylthioalkyl, alkylsulfinylalky, or alkylsulfonylalkyl of 2 to 5 carbon atoms, or amino;
R² is hydrogen or alkyl of 1 to 4 carbon atoms;
X¹ is fluorine or chlorine;
X² is fluorine, chlorine, bromine, alkyl of 1 to 6 carbon atoms, haloalkyl of 1 to 5 carbon atoms, or alkoxy of 1 to 6 carbon atoms; and
Z is

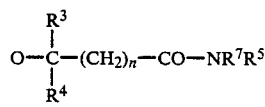

where R³ is H or alkyl of 1 to 4 carbon atoms, R⁴ is H, alkyl of 1 to 4 carbon atoms of alkoxy of 1 to 4 carbon atoms, n is 0 to 2, and —NR⁷R⁵ is the residue of a sulfonamide in which R⁷ is hydrogen, a salt-forming group, or alkyl of 1 to 6 carbon atoms, and R⁵ is alkylsulfonyl, haloalkylsulfonyl, or arylsulfonyl.

9. A compound as in claim 8 in which said arylsulfonamide is a halophenyl, alkoxyphenyl or alkylphenylsulfonamide or a 2,3-dihydrobenzofuranylsulfonamide.

10. An herbicidal composition comprising an herbicidally effective amount of the compound of claim 8 in admixture with a suitable carrier.

11. A method for controlling undesired plant growth which comprises applying to the locus where control is desired an herbicidally effective amount of the composition of claim 10.

12. An herbicidal compound of the formula

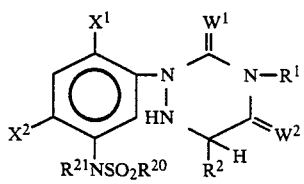

wherein W¹ and W² are independently oxygen or sulfur;
R¹ is alkyl of 1 to 6 carbon atoms, haloalkyl of 1 to 5 carbon atoms, cyanoalkyl of 1 to 5 alkyl carbon atoms, alkenyl or alkynyl of 2 to 5 carbon atoms, alkoxyalkyl, alkylthioalkyl, alkylsulfinylalkyl, or alkylsulfonylalkyl of 2 to 5 carbon atoms, or amino;

$R^2$ is hydrogen or alkyl of 1 to 4 carbon atoms;

$X^1$ is fluorine or chlorine;

$X^2$ is fluorine, chlorine, bromine, alkyl of 1 to 6 carbon atoms, haloalkyl of 1 to 5 carbon atoms, or alkoxy of 1 to 6 carbon atoms;

$R^{20}$ is lower alkyl or haloalkyl of 3 to 5 alkyl carbon atoms, or phenyl which is substituted or unsubstituted with one or more groups selected from halogen, lower alkyl, lower alkoxy, cyano, cyanomethyl, nitro, amino, phenylamino, alkylamino of less than 6 carbon atoms, dialkylamino in which each alkyl is of less than 6 carbon atoms, hydroxycarbonyl, alkoxycarbonyl of less than 6 alkyl carbon atoms, alkoxyalkyl of 2 to 4 carbons atoms, alkoxycarbonylalkyl in which each alkyl is of less than 6 carbon atoms, benzyl, or hydroxy;

$R^{21}$ is hydrogen, a salt-forming group, benzyl, alkyl, haloalkyl, alkoxy, alkynyl or alkenyl each having less than 6 carbon atoms, $SO_2R^{20}$, a group of the formula -alkylene- $SO_2R^{20}$ wherein the alkylene group has 1 to 4 carbon atoms, alkoxymethyl having less than 6 carbon atoms, cyanomethyl, ethoxycarbonylmethyl, or $R^{20}$ and $R^{21}$ together is alkylene of less than 6 carbon atoms.

13. An herbicidal composition comprising an herbicidally effective amount of the compound of claim 12 in admixture with a suitable carrier.

14. A method for controlling undesired plant growth which comprises applying to the locus where control is desired an herbicidally effective amount of the composition of claim 13.

* * * * *